United States Patent [19]

Chibata et al.

[11] 4,090,919
[45] May 23, 1978

[54] WATER-INSOLUBLE TANNIN PREPARATION FOR IMMOBILIZATION OF PROTEINS

[75] Inventors: Ichiro Chibata, Suita; Tetsuya Tosa, Kyoto; Takao Mori, Takatsuki; Taizo Watanabe, Nagaokakyo; Ryujiro Sano, Toyonaka; Yuksi Matuo, Suita, all of Japan

[73] Assignee: Tanabe Seiyaku Co., Ltd., Osaka, Japan

[21] Appl. No.: 760,441

[22] Filed: Jan. 19, 1977

[30] Foreign Application Priority Data

Jan. 29, 1976 Japan ................................ 51-8997
Aug. 27, 1976 Japan ................................ 51-102894
Oct. 30, 1976 Japan ................................ 51-131132

[51] Int. Cl.² .................... C07G 7/02; C07C 69/76; C07G 7/00
[52] U.S. Cl. ........................................ 195/63; 195/68; 195/DIG. 11; 210/36; 260/6; 260/112 R; 426/422; 536/1; 536/32; 536/56; 560/68

[58] Field of Search .................. 195/63, 68, DIG. 11; 426/422; 260/473.5, 112 R, 6, 8; 210/500 M, 36; 536/1, 32, 56; 560/68

[56] References Cited

U.S. PATENT DOCUMENTS

| | | | |
|---|---|---|---|
| 2,650,194 | 8/1953 | Rahn | 260/473.5 X |
| 3,639,558 | 2/1972 | Csizmas et al. | 195/63 X |
| 3,736,231 | 5/1973 | Stanley et al. | 195/63 |
| 3,796,634 | 3/1974 | Haynes et al. | 195/68 X |
| 3,886,066 | 5/1975 | Chen et al. | 210/500 M X |
| 4,008,339 | 2/1977 | Matsuda et al. | 426/422 X |

Primary Examiner—David M. Naff
Attorney, Agent, or Firm—Bierman & Bierman

[57] ABSTRACT

A water-insoluble tannin preparation is obtained by covalent binding or physical adsorption of tannin onto a water-insoluble, hydrophilic carrier. The preparation has a specific affinity for proteins and can be used as an adsorbent for purification, isolation and/or separation of proteins (e.g., Enzymes, albumin, globulin, hormonal proteins) from a mixture of compounds. Further, the water-insoluble tannin preparation having a catalytically active enzyme absorbed thereon can be used as a heterogeneous catalyst to induce enzymatic reactions.

41 Claims, No Drawings

WATER-INSOLUBLE TANNIN PREPARATION FOR IMMOBILIZATION OF PROTEINS

This application claims the priority of Japanese applications 8997/76 filed Jan. 29, 1976, 102894/76 filed Aug. 27, 1976, and 131132/76 filed Oct. 30, 1976.

BACKGROUND OF THE INVENTION

This invention relates to a water-insoluble tannin preparation, biologically active protein immobilized with said tannin preparation, and methods of preparation thereof.

Enzymes and other biologically active proteins isolated from tissues of living organisms (e.g., microbial cells, plants, animal tissues) have been used extensively as, for example, food additives, feed supplements, medicines, chemical reagents and industrial raw materials. Moreover, isolation and purification of proteins have been accomplished by various methods; for example, by precipitating proteins with sodium chloride, ammonium sulfate or organic solvents (e.g., acetone, ethanol) or by absorbing proteins with activated charcoal or clay. Isolation and purification may also be effected by filtering a crude protein solution through the gel of crosslinked dextran or polyacrylamide, or by column chromatography on ion exchange resins. However, the above-mentioned precipitation methods bring about co-precipitation of other high molecular compounds or inorganic materials and sometimes cause partial or total loss of the biological activity of the enzymes due to denaturation thereof. In carrying out the adsorption and chromatographic methods, various organic compounds are adsorbed, together with proteins, onto the adsorbents or ion exchange resins employed. For this reason, proteins recovered by these methods are usually contaminated with ingredients other than proteins. The gel-filtration may be useful to recover proteins in a high purity without contamination with low molecular compounds, but gel-filtration is a laborious technique and it is difficult to filter a large amount of crude protein solution through the gel.

On the other hand, immobilized enzymes (i.e., enzymes bound to carriers) have become of importance in recent years [Annual Review of Biochemistry, Vol. 35, Part II, P. D. Beyer, Editor; Annual Review Inc., Palo Alto, Calif.; pages 873–908; 1966]. Said immobilized enzymes can be used as heterogeneous catalysts in suspension or column form and, after the reactions are completed, may be readily removed from the reaction mixtures. Further, the immobilized enzymes may be used repeatedly to induce specific chemical changes in large amounts of substrate. In this connection, various methods for immobilization of enzymes have been known, including (a) covalent binding of the enzymes to suitable water-insoluble carriers such as haloacetyl-polysaccharides; (b) ionic binding to carriers such as diethylaminoethyl-(DEAE) cellulose or DEAE-Sephadex; (c) physical adsorption on inert carriers or synthetic ion exchange resins; (d) covalent cross-linking of the enzymes by bifunctional agents; (e) inclusion within the gel lattice of polyacrylamide; and (f) microencapsulation of the enzymes with semipermeable nylon membranes. Method (c) has been conducted by physically adsorbing enzymes on activated carbon or porous glass [U.S. Pat. No. 2717852, Enzymologia, 39, 12 (1970)]. These known methods (c) afford, by simple operations, the immobilized preparations having a high enzymatic activity. In said known cases, however, partial or total desorption of the enzymes is brought about even under mild conditions; for example, by changing pH or temperatures or by addition of a substrate.

SUMMARY OF THE INVENTION

It has now been found that a water-insoluble tannin preparation, i.e. tannin bound to a carrier by covalent linkage or physical adsorption, shows a strong ability to bind proteins specifically and reversibly, and is useful as an adsorbent for concentration of dilute protein solutions. The water-insoluble tannin preparation is also useful as an adsorbent for selective removal of protein contaminants from a mixture of various compounds. Further, a water-insoluble tannin preparation having a catalytically active enzyme adsorbed thereon is useful as a heterogeneous catalyst to induce chemical or enzymatic reactions. Enzymes are firmly adsorbed on the tannin preparation without substantial denaturation and no detectable desorption of the enzymes occurs under the conditions of enzymatic reactions or even on addition of an excess of substrates.

An object of the present invention is to provide a water-insoluble tannin preparation which shows special and unique affinity for proteins and is useful as an adsorbent therefor. Another object of the invention is to provide an adsorbent which is useful for selective isolation, purification or separation of proteins and even for selective removal of protein contaminants from a mixture of compounds. A further object is to provide a method of preparing the insoluble tannin preparation. A still further object is to provide a novel immobilized enzyme which affords high enzymatic activity for a long period of time, and at the same time allows reuse thereof in a number of successive operations. Further objects of the present invention will be apparent from the descriptions which follow.

Throughout the specifications, $\text{\textcircled{T}}_{-OH}{-}^{OH}$ and $\text{\textcircled{T}}{-}OH$ stand for tannin, $\text{\textcircled{P}}_{-OH}{-}^{OH}$, $\text{\textcircled{P}}_{-OH}{-}^{OH}$, $\text{\textcircled{P}}{-}OH$ and $\text{\textcircled{P}}{-}OH$ stand for hydroxy-polymers, $\text{\textcircled{P}}{-}NH_2$ and $\text{\textcircled{P}}{-}NH_2$ stand for amino-polymers, and $\text{\textcircled{P}}{-}COOH$ and $\text{\textcircled{P}}{-}COOH$ stand for carboxyl-polymers. Further each one of $n$ and $m$ is an integer of 1 to 16, and A is a group of the formula: $-(CH_2)_q-$ or $-O(CH_2)_qO-$, wherein $q$ is an integer of 1 to 6. The relevant reactions are as follows:

ACTIVATION OF HYDROXY-AND AMINO-POLYMERS

Reaction 1

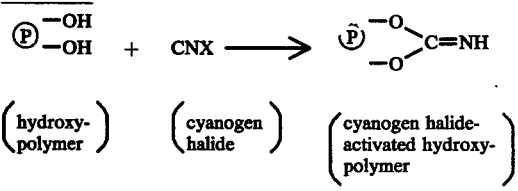

$$\text{\textcircled{P}}{\overset{-OH}{-OH}} + CNX \longrightarrow \text{\textcircled{P}}{\overset{-O}{-O}}{>}C{=}NH$$

(hydroxy-polymer) (cyanogen halide) (cyanogen halide-activated hydroxy-polymer)

4,090,919

-continued

Reaction 2

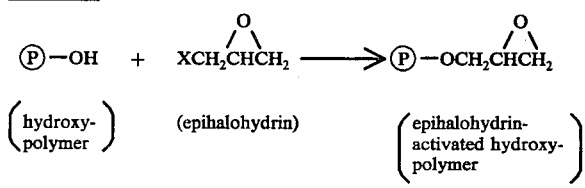

(hydroxy-polymer)   (epihalohydrin)   (epihalohydrin-activated hydroxy-polymer)

Reaction 3

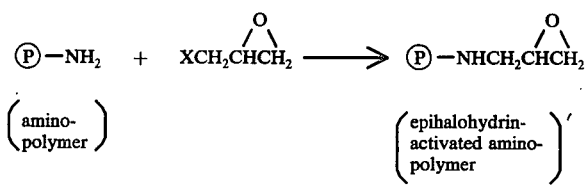

(amino-polymer)     (epihalohydrin-activated amino-polymer)

Reaction 4

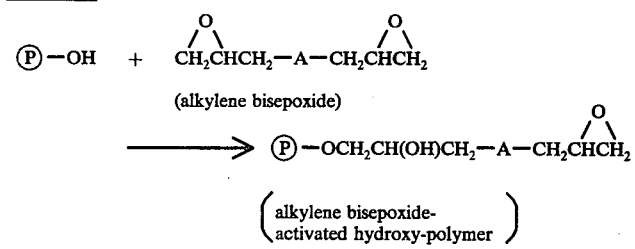

(alkylene bisepoxide)

(alkylene bisepoxide-activated hydroxy-polymer)

Reaction 5

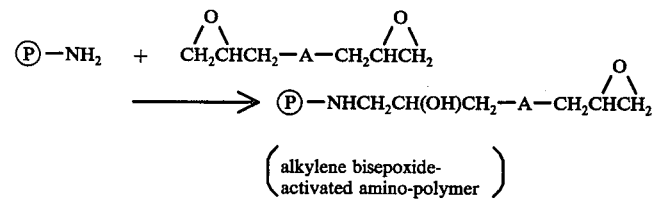

(alkylene bisepoxide-activated amino-polymer)

Reaction 6

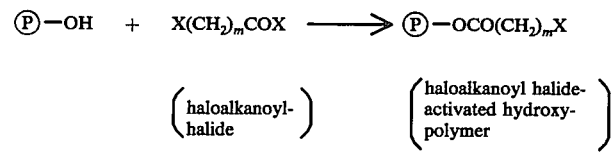

(haloalkanoyl-halide)   (haloalkanoyl halide-activated hydroxy-polymer)

ACTIVATION OF TANNIN

Reaction 7

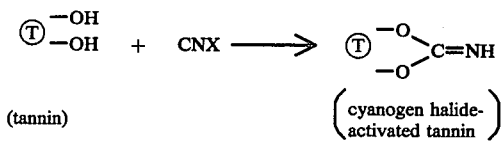

(tannin)   (cyanogen halide-activated tannin)

Reaction 8

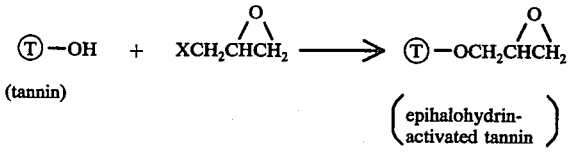

(tannin)   (epihalohydrin-activated tannin)

Reaction 9

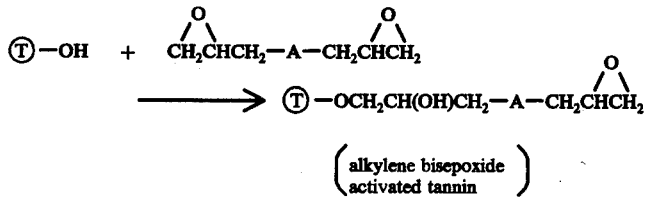

(alkylene bisepoxide activated tannin)

SYNTHESIS OF HYDROXY-POLYMERS

Reaction 10

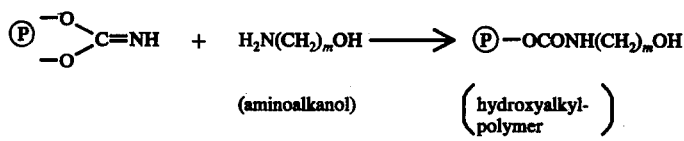

(aminoalkanol)    (hydroxyalkyl-polymer)

Reaction 11

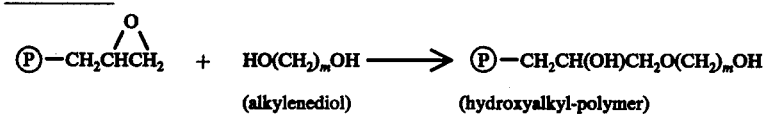

(alkylenediol)    (hydroxyalkyl-polymer)

SYNTHESIS OF AMINO-POLYMERS

Reaction 12

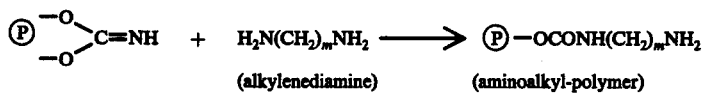

(alkylenediamine)    (aminoalkyl-polymer)

Reaction 13

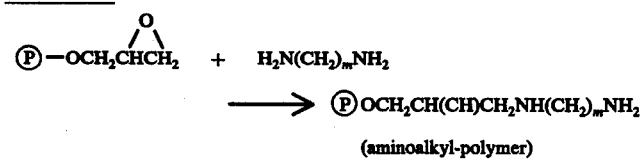

(aminoalkyl-polymer)

Reaction 14

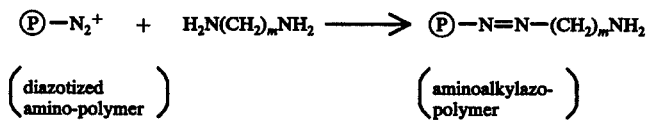

(diazotized amino-polymer)    (aminoalkylazo-polymer)

Reaction 15

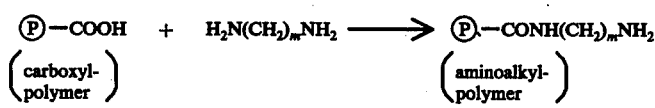

(carboxyl-polymer)    (aminoalkyl-polymer)

SYNTHESIS OF CARBOXYL-POLYMERS

Reaction 16

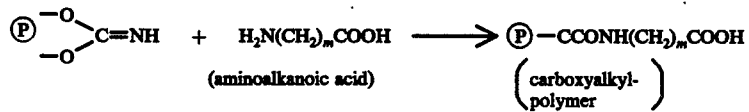

(aminoalkanoic acid)    (carboxyalkyl-polymer)

Reaction 17

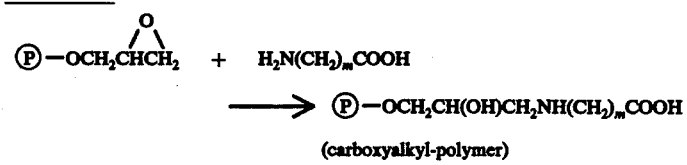

(carboxyalkyl-polymer)

Reaction 18

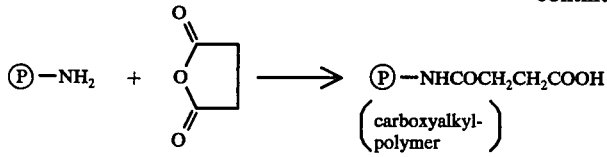
Reaction 19
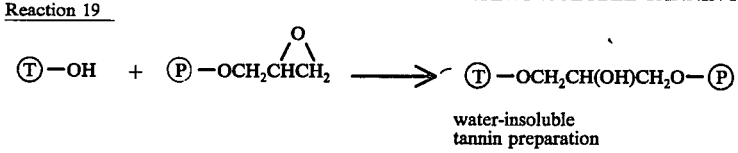
SYNTHESIS OF WATER-INSOLUBLE TANNIN PREPARATIONS
Reaction 20
Reaction 21
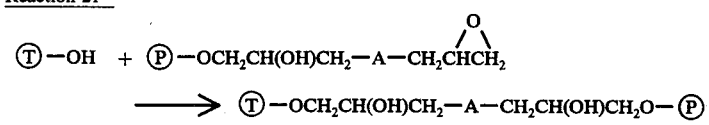
Reaction 22
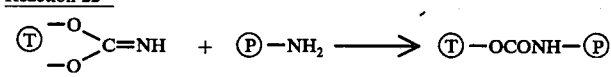
Reaction 23
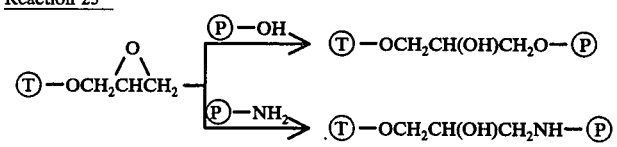
Reaction 24
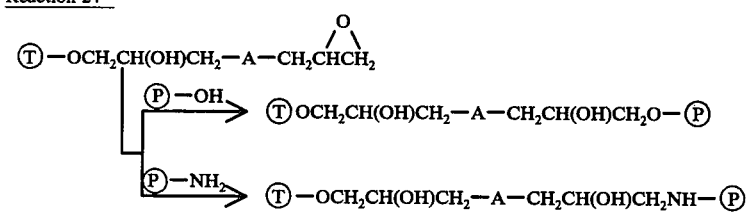
Reaction 25
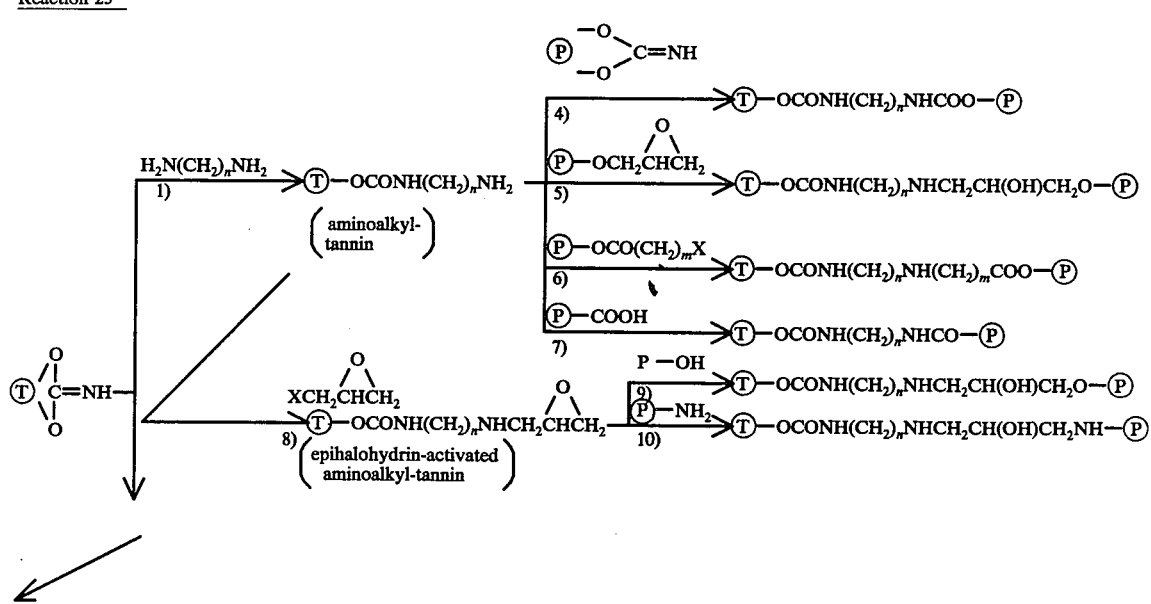

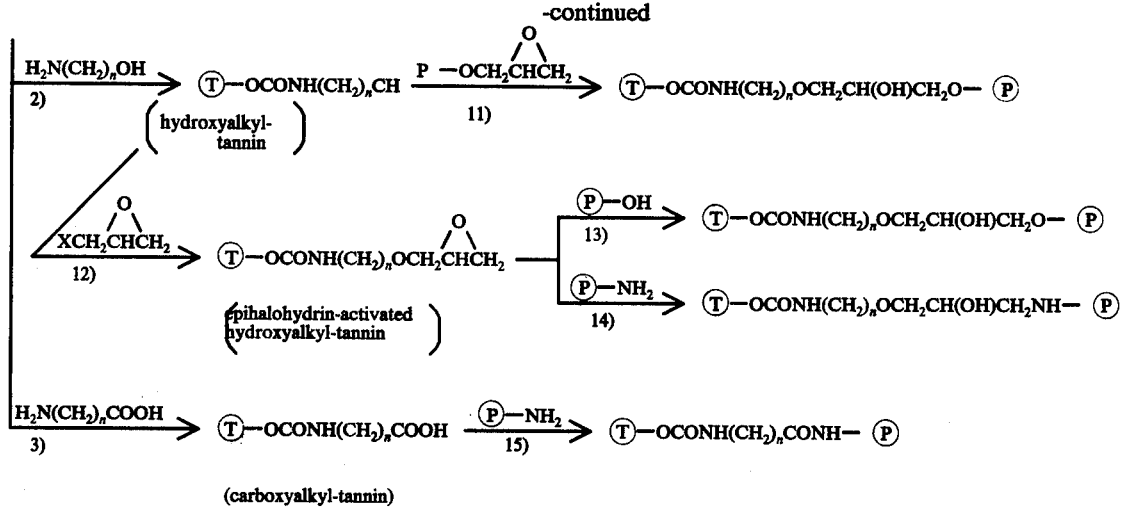
Reaction 26
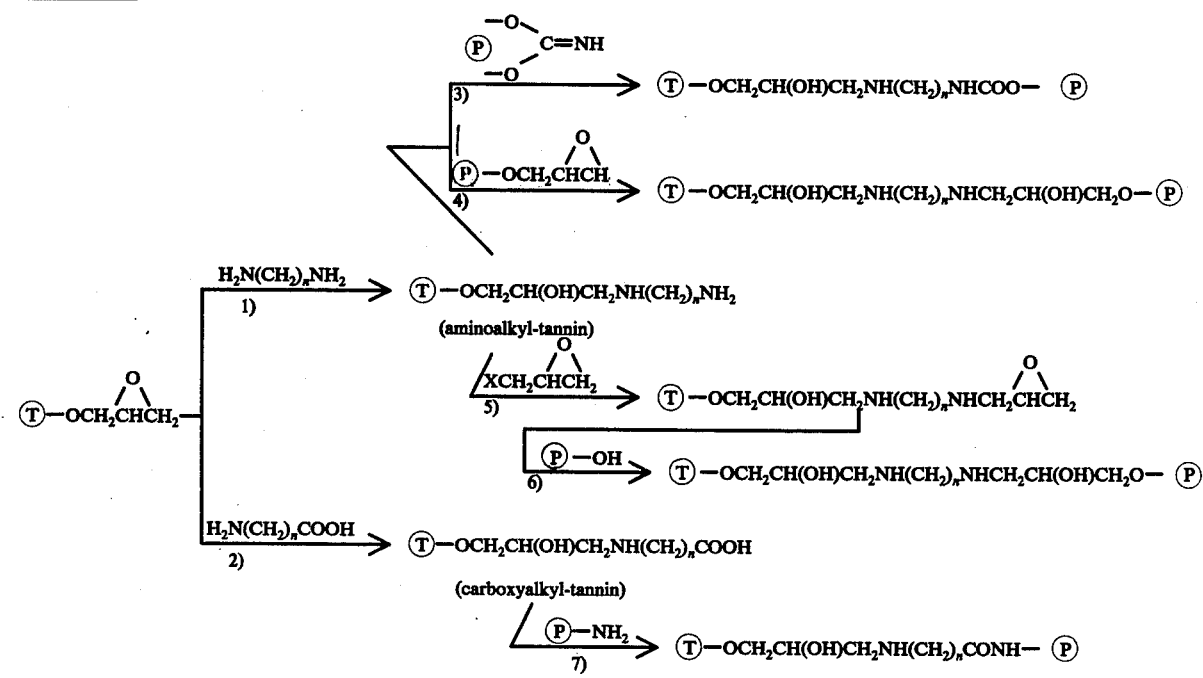
Reaction 27
$\text{T}-\text{OH} + \text{P}-\text{NH}_2^+ \longrightarrow \text{T}-\text{N}=\text{N}-\text{P}$
(diazotized amino-polymer)
SYNTHESIS OF ALKYL-POLYMERS
Reaction 28
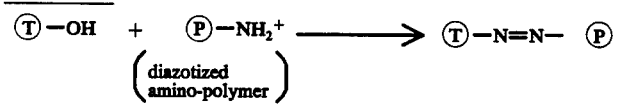
(cyanogen halide-activated hydroxy-polymer)     (alkyl-polymer)
Reaction 29
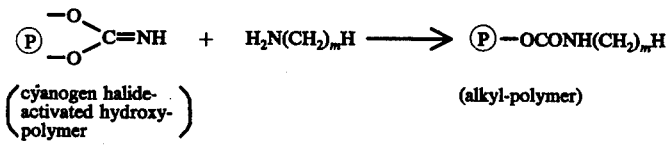
epihalohydrin-activated hydroxy-polymer     (alkyl-polymer)
Reaction 30

-continued

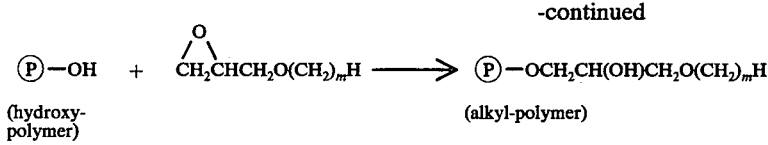

SYNTHESIS OF PHENOXYALKYL-POLYMER

Reaction 31

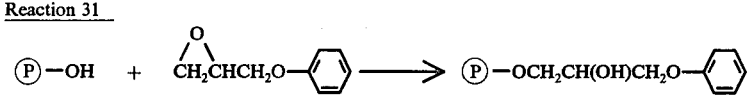

DESCRIPTION OF THE INVENTION INCLUDING PREFERRED EMBODIMENTS

According to the present invention, the water-insoluble tannin preparation can be prepared by covalently binding or physically adsorbing tannin onto a water-insoluble, hydrophilic carrier. More particularly, said tannin preparation is prepared either by binding tannin and the water-insoluble, hydrophilic carrier through at least one divalent functional group, or by simply contacting the tannin with the water-insoluble, hydrophilic carrier.

The term "Hydrophilic" as used herein means that the polymer is made wettable or swellable in water but not substantially soluble therein. Various polymers having these properties may be employed in the present invention. Such polymers include, for example, polymers having hydroxy, amino, carboxyl, alkyl or phenoxyalkyl groups (i.e., hydroxy-polymers, amino-polymers, carboxyl-polymers, alkyl-polymers and phenoxyalkyl-polymers). Polysaccharides such as cellulose, agarose and cross-linked dextran (e.g. dextran cross-linked with epichlorohydrin or divinylsulphone) are suitable as the hydroxy-polymers.

In the present invention, however, such hydroxy-polymers may be modified, prior to the binding of tannin thereto, with at least one bifunctional reagent to give other suitable hydroxy-polymers. For example, the hydroxy-polymers such as polysaccharides are treated with cyanogen halide (e.g., cyanogen bromide) or epihalohydrin (e.g., epichlorohydrin), and the cyanogen halide - or epihalohydrin-activated hydroxy-polymers obtained are then reacted with aminoalkanols (e.g., aminomethanol, aminoethanol, aminopropanol) or alkylenediol (e.g., methyleneglycol, ethyleneglycol, tetramethyleneglycol, hexamethyleneglycol), respectively. The thus-obtained hydroxyalkyl-polymers such as hydroxyalkyl-polysaccharides can also be used as the hydroxy-polymers of the present invention.

The activation reaction of the hydroxy-polymers with cyanogen halide or epihalohydrin [Reactions (1 and 2)] may be carried out at 4° to 40° C. at pH 8 to 12 (if cyanogen halide is used), or at 30° to 100° C. at pH 9 to 14 (if epihalohydrin is used), in an aqueous solvent (e.g., water). When cellulose is used as the hydroxy-polymer, it is preferred to treat the polymer with an alkali metal hydroxide (e.g., sodium hydroxide) prior to the reaction with cyanogen halide or epihalohydrin. The reaction of the cyanogen halide-activated hydroxy-polymers with aminoalkanols [Reaction 10] may be carried out at 4° to 40° C. at pH 8 to 12 in an aqueous solvent (e.g., water) and the reaction of the epihalohydrin-activated hydroxy-polymer with alkylenediols [Reaction 11] may be carried out at 30° to 100° C. at pH 9 to 14 in an aqueous solvent (e.g., water).

Suitable examples of the amino-polymer include aminobenzyl-polysaccharide (e.g., p-aminobenzyl-cellulose), cross-linked polyacrylamide (e.g., polyacrylamide cross-linked with N,N'-methylenebisacrylamide), cross-linked p-aminophenyl-polyacrylamide (e.g., p-aminophenyl-polyacrylamide cross-linked with N,N'-methylenebisacrylamide), cross-linked p-aminobenzamidoethyl-polyacrylamide (e.g., p-aminobenzamidoethyl-polyacrylamide cross-linked with N,N'-methylenebisacrylamide), p-aminobenzamido-porous glass, p-aminophenylalanine-leucine copolymer, p-aminopolystyrene, methacrylic acid-m-aminostyrene copolymer, aminoalkylscleroprotein (e.g., aminohexyl-wool, aminohexyl-silk) and cross-linked aminoalkyl-polymethacrylic acid (e.g., aminohexyl-polystyrene cross-linked with divinylbenzene).

Amino-polymers which are prepared from hydroxy-polymers by the use of suitable bifunctional reagents may also be used in the present invention. For example, the reaction of alkylenediamines with cyanogen halide-activated hydroxy-polymers or the reaction of alkylenediamines with epihalohydrin-activated hydroxy-polymers yields the corresponding aminoalkyl-polymers which may be employed as the amino-polymers of the present invention. Preferred examples of such aminoalkyl-polymers include aminoalkyl-polysaccharides such as aminoethyl-cellulose, aminobutyl-cellulose, aminohexyl-cellulose, aminooctyl-cellulose, aminododecyl-cellulose, aminoethyl-agarose and aminohexyl-agarose. The reaction of alkylenediamines with cyanogen halide-activated hydroxy-polymers [Reaction 12] may be carried out at 4° to 40° C at pH 8 to 12 in an aqueous solvent (e.g., water), and various alkylenediamines such as ethylenediamine, tetramethylenediamine, hexamethylenediamine, octamethylenediamine, decamethylenediamine and dodecamethylenediamine may be employed for said reaction. The reaction of alkylenediamines with the epihalohydrin-activated hydroxy-polymers [Reaction 13] may be carried out at 30° to 100° C. at pH 9 to 14 in an aqueous solvent (e.g., water).

Moreover, the amino-polymers of the present invention may be prepared by reacting alkylenediamine with diazotized amino-polymers such as diazotized p-aminobenzyl-cellulose or diazotized p-aminophenyl-polyacrylamide cross-linked with N,N'-methylenebisacrylamide, or by reacting alkylenediamines with carboxyl-polymers such as carboxymethyl-polysaccharide. By this reaction, an aminoalkyl-polysaccharide having the formula (P)-OCH$_2$CONH(CH$_2$)$_m$NH$_2$ may be obtained from the carboxymethyl-polysaccharide.

The reaction of alkylenediamines with diazotized amino-polymers [Reaction 14] may be carried out at 4° to 20° C at pH 7.5 to 10 in an aqueous solvent (e.g., water). On the other hand, the reaction of alkylenediamines with carboxyl-polymers [Reaction 15] may be carried out by treating them at 4° to 40° C in the presence of a carbodiimide reagent (e.g., 1-ethyl-3-(3-dimethyl-aminopropyl) carbodiimide, 1-cyclohexyl-3-(2-morpholinoethyl) carbodiimide) or a Woodward reagent (i.e., 2-ethyl-5-m-sulfophenyl-isoxazolium hydroxide) in a suitable solvent. The reaction of alkylenediamines with the carboxyl-polymers may also be carried out by converting the carboxylpolymers into the corresponding reactive derivatives (e.g., acid azide, acid halide, N-hydroxy-succinimide ester), and then reacting the reactive derivatives with the alkylenediamines.

Examples of polymers having carboxyl group (i.e., carboxyl-polymers) include cross-linked polymethacrylic acid such as polymethacrylic acid cross-linked with divinylbenzene; cross-linked carboxymethyl-polyacrylamide such as carboxymethyl-polyacrylamide cross-linked with N,N'-methylenebisacrylamide; and carboxyalkyl-polysaccharides such as carboxymethyl-cellulose, carboxyethyl-cellulose, carboxybutyl-cellulose, carboxyhexyl-cellulose, carboxymethyl-agarose, carboxyethyl-agarose, carboxybutyl-agarose or carboxyhexyl-agarose. The carboxyalkyl-polysaccharides may be prepared by reacting the cyanogen halide - or epihalohydrin-activated polysaccharides with aminoalkanoic acid such as aminoacetic acid, aminopropionic acid, aminohexanoic acid, or aminoheptanoic acid. Said reaction [Reactions 16 & 17] may be readily conducted at 4° to 40° C at pH 8 to 12 (if cyanogen halide-activated polysaccharide is used) or at 30° to 100° C at pH 9 to 14 (if epihalohydrin-activated polysaccharide is used) in an aqueous solvent (e.g., water). Alternatively, the carboxyalkyl-polysaccharides may be prepared by reacting amino-polymers with succinic acid anhydride [Reaction 18]. This reaction may be carried out at 4° to 40° C at pH 4.5 to 6 in an aqueous solvent (e.g., water). Other examples of the water-insoluble, hydrophilic carrier which may be used in the present invention include fibrous scleroproteins such as wool or silk. These scleroproteins contain both amino groups and carboxyl groups in their molecules, and can be used as either the amino-polymer or the carboxyl-polymer.

"Tannin" is the general term for astringent, aromatic, acidic glucosides of polyphenols found in various plants and trees and, depending on the structure thereof, can be divided into two groups: (a) pyrogallol tannin (i.e., mono-, di- and/or trigalloyl monosaccharides, mono-, di- and/or trigalloyl disaccharides, and mono-, di- and-/or trigalloyl trisaccharides); and (b) catechol tannin (i.e., polyhydroxyphenol condensates and polyhydroxy-flavan condensates). Examples of pyrogallol tannin include gallotannin, pentagalloyl glucose, Hamameli tannin and Acetannin. Examples of catechol tannin are polycatechol, polyepicatechol, polycatechin, polycatechin, poly (pistacia catechol) and poly(galloyl epicatechol). All of these pyrogallol and catechol tannins can be employed in the present invention. For making the water-insoluble tannin preparation, however, these tannins need not necessarily be in pure form, but crude products obtained from plants and trees may be employed without purification. For example, crude pyrogallol tannins such as chinese gallotannin or nutgalls-tannin and crude catechol tannins such as persimmon tannin are preferably used for the purposes of the present invention.

According to one embodiment of the present invention, the water-insoluble tannin preparation is prepared by reacting either tannin or the water-insoluble, hydrophilic carrier (said carrier being either a hydroxy-polymer or an amino-polymer) with at least one bifunctional reagent to give an activated tannin or carrier, and then reacting said activated tannin or carrier with the carrier or tannin. The bifunctional reagents may be either (i) a "homo" bifunctional reagent possessing two identical functional groups, such as alkylene bisepoxide; or (ii) a "hetero" bifunctional reagent possessing two different functional groups, such as cyanogen halide epihalohydrin or haloalkanoyl halide.

Examples of the bifunctional reagents which may be used for activation of tannin and the hydroxy-polymer include cyanogen halide, epihalohydrin and alkylene bisepoxide such as α,ω-bis (2,3-epoxypropyl) alkane or α,ω-bis(2,3-epoxypropoxy) alkane. The epihalohydrin and alkylene bisepoxide may also be used for activation of the amino-polymer. Further, haloalkanoyl halide may be employed for activation of the hydroxy-polymer. Examples of cyanogen halide and epihalohydrin include cyanogen chloride, cyanogen bromide, epichlorohydrin and epibromohydrin. Preferred examples of the alkylene bisepoxide (i.e., a compound of the formula

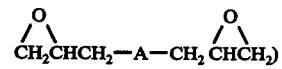

include those having 1 to 12 carbon atoms such as α,ω-bis(2,3-epoxypropyl) ethane, α,ω-bis(2,3-epoxypropyl) butane or α,ω-bis(2,3-epoxypropoxy) butane. Preferred examples of the haloalkanoyl halide (i.e., a compound of the formula $X(CH_2)_m COX$, wherein X is halogen) include those having 2 to 16 carbon atoms such as chloroacetyl chloride or bromoacetyl bromide.

In making the water-insoluble tannin preparation of the invention, either tannin or the hydroxy - or amino-polymer may be activated first. When illustrating these activation and subsequent coupling reations by taking into account the reaction formulae shown herein, the activation of tannin or the hydroxy-polymer with cyanogen halide [Reactions 1 and 7] may be carried out at 4° to 40° C at pH 8 to 12 in an aqueous solvent (e.g., water). On the other hand, the activation of tannin or the hydroxy - or amino-polymer with epihalohydrin or alkylene bisepoxide [Reactions 2, 3, 4, 5, 8 and 9] may be carried out at 30° to 70° C at pH 8 to 12 in an aqueous solvent (e.g., water). The activation reaction of the hydroxy-polymer with the haloalkanoyl halide [Reaction 6] may be carried out at 4° to 40° C in an aqueous solvent (e.g., water). The reaction of tannin with the epihalohydrin - or alkylene bisepoxide-activated hydroxy - or amino-polymer thus obtained [Reactions 19, 20 and 21] yields a water-insoluble tannin preparation in which tannin is covalently bound to the hydroxy - or amino-polymer through the linkage —CH$_2$CH(OH)CH$_2$ — or —CH$_2$CH(OH)CH$_2$ —A—CH$_2$CH(OH)CH$_2$—.

Similarly, the reaction of epihalohydrin - or alkylene bisepoxide-activated tannin with the hydroxy - or amino-polymer [Reactions 23 and 24] affords a tannin preparation in which tannin is covalently bound to the hydroxy - or amino-polymer through the linkage: —CH$_2$CH(OH)CH$_2$ — or —CH$_2$CH(OH)CH$_2$—A—CH$_2$CH (OH)CH$_2$—. More specifically, for example, a water-insoluble tannin preparation in which tannin is bound to polysaccharide through the linkage: —CH$_2$CH(OH)CH$_2$—, —CH$_2$CH(OH)CH$_2$ —

A—CH$_2$CH(OH)CH$_2$ — or —CH$_2$CH(OH)CH$_2$NH(CH$_2$)$_n$—Y— (Y is a group of the formula: —NHCO—, NHCH$_2$CH(OH)CH$_2$—, —OCH$_2$CH(OH)CH$_2$ — or —NHCOCH$_2$—) may be prepared from polysaccharide, the aminoalkyl-polysaccharide shown in Reactions 12 and 13 or the aminoalkyl-polysaccharide of the formula: (p)—OCH$_2$CONH(CH$_2$)$_n$NH$_2$ by using them as the hydroxy- or amino-polymers shown in Reactions 19, 21 and 23 respectively. The reaction of tannin with the epihalohydrin or alkylene bisepoxide-activated hydroxy- or amino-polymer may be carried out at 30° to 70° C at pH 8 to 12 in an aqueous solvent (e.g., water). The reaction of epihalohydrin- or alkylene bisepoxide-activated tannin with the hydroxy- or amino-polymer may be carried out at 30° to 70° C at pH 8 to 12 in an aqueous solvent (e.g., water). Alternatively, a tannin preparation in which tannin is covalently bound to the amino-polymer through the linkage —CONH— may be prepared by reacting cyanogen halide-activated tannin with the amino-polymer [Reaction 22]. For example, tannin bound to polysaccharide through the linkage —CONH(CH$_2$)$_n$—Y —(Y is the same as defined above) may be obtained from the aminoalkyl-polysaccharides shown in Reactions 12 or 13 or those of the formula: (p)—OCH$_2$CONH(CH$_2$)$_n$NH$_2$. The reaction of the amino-polymer with cyanogen halide-activated tannin may be carried out at 4° to 40° C at pH 4.5 to 6 in an aqueous solvent (e.g., water).

In order to make the water-insoluble tannin preparation, the above-mentioned bifunctional reagents such as cyanogen halide, epihalohydrin, alkylene bisepoxide and haloalkanoyl halide may be used in combination with at least one of other bifunctional reagents such as alkylenediamine, aminoalkanol or aminoalkanoic acid. That is, the water-insoluble tannin preparation can be prepared from the activated tannin [i.e. tannin activated with cyanogen halide, epihalohydrin, α,ω-bis(2,3-epoxypropyl)alkane or α,ω-bis(2,3-epoxypropoxy) alkane] by reacting it with alkylenediamine or aminoalkanol to give an aminoalkyl- or hydroxyalkyl-tannin, reacting either the tannin derivative or the hydroxy- or amino-polymer with cyanogen halide, epihalohydrin, α,ω-bis(2,3-epoxypropyl) alkane α,ω-bis(2,3-epoxypropoxy) alkane or haloalkanoyl halide to give an activated tannin derivative or polymer, and then reacting the activated tannin derivative with the hydroxy- or amino-polymer; or the activated polymer with the aminoalkyl - or hydroxyalkyl-tannin. The water-insoluble tannin preparation can also be prepared by condensing the aminoalkyl-tannin with the carboxyl-polymer. Alternatively, the water-insoluble tannin preparation may be prepared by reacting tannin with cyanogen halide, epihalohydrin, α,ω-bis(2,3-epoxypropyl) alkane or α,ω-bis(2,3-epoxypropoxy)alkane to give an activated tannin, reacting said activated tannin with aminoalkanoic acid to give a carboxyalkyl-tannin, and then reacting the carboxyalkyl-tannin with the amino-polymer.

To illustrate these reactions more specifically, the cyanogen halide-activated tannin is reacted with the alkylenediamine, aminoalkanol or aminoalkanoic acid to give the corresponding aminoalkyl-, hydroxyalkyl- or carboxyalkyl-tannin [Reactions 25-1, 25-2 and 25-3]. The aminoalkyl-tannin and carboxyalkyl-tannin may also be prepared by reacting the epihalohydrin-activated tannin with the alkylenediamine or aminoalkanoic acid, respectively [Reactions 26-1 and 26-2]. Examples of the alkylenediamine [i.e., a compound of the formula: H$_2$N(CH$_2$)$_n$NH$_2$ or H$_2$N(CH$_2$)$_m$NH$_2$] include those having 1 to 16 carbon atoms such as ethylenediamine, tetramethylenediamine, hexamethylenediamine, octamethylenediamine, decamethylenediamine and dodecamethylenediamine. Examples of the aminoalkanol [i.e., a compound of the formula: H$_2$N(CH$_2$)$_n$OH or H$_2$N(CH$_2$)$_m$OH] include those having 1 to 16 carbon atoms such as aminoethanol, aminopropanol, aminobutanol or aminopentanol. Examples of the aminoalkanoic acid [i.e., H$_2$N(CH$_2$)$_n$COOH or H$_2$N(CH$_2$)$_m$COOH] include those having 2 to 16 carbon atoms such as aminoacetic acid, aminopropionic acid, aminohexanoic acid or aminoheptanoic acid.

A water-insoluble tannin preparation in which tannin is bound to the hydroxy-polymer through the linkage —Y'—(CH$_2$)$_n$NHCO—, —Y'—(CH$_2$)$_n$NHCH$_2$CH(OH)CH$_2$— or —Y'—(CH$_2$)$_n$NH(CH$_2$)$_m$CO— (Y' is a group of the formula —CONH— or CH$_2$CH(OH)CH$_2$NH—) may be prepared by further reacting the resultant aminoalkyl-tannin with a cyanogen halide-, epihalohydrin- or haloalkanoyl halide-activated hydroxy-polymer [Reactions 25-4, 25-5, 25-6, 26-3 and 26-4]. On the other hand, a water-insoluble tannin preparation in which tannin is covalently bound to the hydroxy-polymer through the linkage —CONH(CH$_2$)$_n$OCH$_2$CH(OH)CH$_2$— may be obtained by reacting the hydroxyalkyl-tannin with the epihalohydrin-activated hydroxy-polymer [Reaction 25-11]. Alternatively, a tannin preparation in which tannin is covalently bound to the carboxyl-polymer or amino-polymer through the linkage —Y'—(CH$_2$)$_n$NHCO— or —Y'—(CH$_2$)$_n$CONH— (Y' is the same as defined above) may be obtained by reacting the aminoalkyl-tannin or carboxyalkyl tannin obtained above with the carboxyl-polymer or amino-polymer [Reactions 25-7, 25-15 and 26-7]. The reaction of cyanogen halide-activated tannin with the alkylenediamine, aminoalkanol or aminoalkanoic acid may be carried out at 4° to 40° C at pH 8 to 12 in an aqueous solvent (e.g., water), and the reaction of epihalohydrin-activated tannin with the alkylenediamine or aminoalkanoic acid may be carried out at 30° to 70° C at pH 8 to 12 in an aqueous solvent (e.g., water). The reaction of the aminoalkyl-tannin with the cyanogen halide- or epihalohydrin-activated hydroxy-polymer may be carried out in the same manner as in case of Reactions 22 and 23, respectively. Tannin bound to polysaccharide through the linkage —Y'—(CH$_2$)$_n$NHCO— or —Y'—(CH$_2$)$_n$NHCH$_2$CH(OH)CH$_2$—(Y' is the same as defined above) may be obtained by using cyanogen halide-activated polysaccharide or epihalohydrin-activated polysaccharide as the activated polymer in Reactions 25-4, 25-5, 26-3 and 26-4. The reaction of the aminoalkyl-tannin with the haloalkanoyl halide-activated hydroxy-polymer may be carried out at 4° to 40° C in an aqueous solvent (e.g., water). The reaction of the hydroxy alkyl-tannin with the epihalohydrin-activated hydroxy-polymer may be carried out in the same manner as in case of Reaction 23, and tannin bound to polysaccharide through the linkage —CONH—(CH$_2$)$_n$OCH$_2$CH(OH)CH$_2$— is thereby obtained from epihalohydrin-activated polysaccharide. The condensation reaction of the aminoalkyl-tannin or carboxyalkyl-tannin with the carboxyl-polymer or amino-polymer may be carried out at 4° to 40° C in the presence of a carbodiimide reagent [e.g., 1-ethyl-3-(3-dimethyl-aminopropyl) carbodiimide, 1-cyclohexyl-3-(2-morpholinoethyl) carbodiimide] or Woodward reagent (i.e., 2-ethyl-5-m- sulfenyl-isoxazolium hydroxide) in a solvent (e.g., water). Said condensation reaction may also be carried out by converting the carboxyalkyl-tannin or carboxyl-polymer into the corresponding reactive derivative (e.g., acid azide, acid halide, N-hydroxy-succinimide ester) and then treating the reactive derivative with the amino-polymer or aminoalkyl-tannin. Furthermore, a water-insoluble tannin preparation in which tannin is covalently bound to the hydroxy- or amino-polymer through the linkage —Y′—(CH$_2$)$_n$NHCH$_2$CH(OH)CH$_2$— or —CONH(CH$_2$)$_n$ OCH$_2$CH(OH)CH$_2$— (Y′ is the same as defined above) may be prepared by reacting the aminoalkyl-tannin or hydoxyalkyl-tannin with epihalohydrin to give the corresponding epihalohydrin-activated aminoalkyl- or hydroxyalkyl-tannin [Reactions 25-8, 25-12 and 26-5], and then reacting the activated tannin derivative with the hydroxy-polymer or amino-polymer [Reactions 25-9, 25-10, 25-13, 25-14 and 26-6]. Said reaction of the aminoalkyl- or hydroxyalkyl-tannin with epihalohydrin may be carried out in the same manner as in Reaction 8. On the other hand, the reaction of epihalohydrin-activated aminoalkyl- or hydroxyalkyl-tannin with the hydroxy- or amino-polymer may be carried out in the same manner as in Reaction 23. Tannin bound to polysaccharide through the linkage —CONH— (CH$_2$)$_n$NHCH$_2$CH(OH)CH$_2$—, —CONH(CH$_2$)$_n$OCH$_2$CH(OH)CH$_2$— or —CH$_2$CH(OH)CH$_2$NH(CH$_2$)$_n$NHCH$_2$CH(OH)CH$_2$— may be obtained by using polysaccharide as the hydroxy-polymer in Reactions 25-9, 25-13, and 26-6.

When the amino-polymer is employed as the water-insoluble carrier of the invention, tannin may be bound to the carrier without using any bifunctional reagents mentioned hereinbefore. For example, tannin can be directly bound to the carrier through a diazo group by diazotization of the amino-polymer with an alkali metal nitrite (e.g., sodium nitrite), followed by reacting said diazotized amino-polymer with tannin. The diazotization can be carried out at 0° to 20° C in an aqueous solvent (e.g., water) under acidic conditions, and the condensation reaction of the diazotized amino-polymer with tannin [Reaction 27] may be carried out at 4° to 20° C at pH 7.5 to 10 in an aqueous solvent (e.g., water). A tannin preparation in which tannin is covalently bound to polysaccharide through the linkage

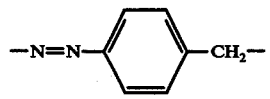

may be obtained by using aminobenzyl-polysaccharide as the amino-polymer.

According to another embodiment of the present invention, the water-insoluble tannin preparation is prepared by adsorbing tannin on a water-insoluble, hydrophilic carrier. The hydroxy-polymers, amino-polymers, carboxyl-polymers, alkyl-polymers and phenoxyalkyl-polymers described hereinbefore may be used for this purpose. Among them, aminoalkyl-polysaccharides, hydroxyalkyl-polysaccharides, carboxyalkyl-polysaccharides, alkyl-polysaccharides and phenoxyalkyl-polysaccharides [i.e., polysaccharides having a group of the formula —(CH$_2$)$_m$R, wherein R is hydrogen, phenoxy, amino, hydroxy or carboxyl and $m$ is an integer of one to 16] are especially suitable for the physical adsorption of tannin. The aminoalkyl-polysaccharides, hydroxyalkyl-polysaccharides and carboxyalkyl-polysaccharides may be prepared in the same manner as described hereinbefore.

On the other hand, the alkyl-polysaccharide (e.g., methyl-polysaccharide, ethyl-polysaccharide, propyl-polysaccharide, butyl-polysaccharide, hexyl-polysaccharide, octyl-polysaccharide, decyl-polysaccharide, dodecyl-polysaccharide) may be prepared by (i) reacting a cyanogen halide-activated polysaccharide or epihalohydrin-activated polysaccharide with an alkylamine having one to 16 carbon atoms (e.g., methylamine, ethylamine, propylamine, butylamine, hexylamine, octylamine, decylamine, dodecylamine); or (ii) reacting polysaccharide with an alkyl glycidyl ether (e.g., methyl, ethyl, propyl, butyl, hexyl, octyl, decyl or dodecyl ether of 2,3-epoxypropanol). Cellulose, agarose and cross-linked dextran are suitable as the polysaccharide. The phenoxyalkyl-polysaccharide may be prepared by reacting polysaccharide with phenyl glycidyl ether (i.e., phenyl ether of 2,3-epoxypropanol). The reaction of cyanogen halide-activated polysaccharide or epihalohydrin-activated polysaccharide with the alkylamine [Reactions 28 and 29] may be carried out at 4° to 40° C at pH 8 to 12 (if cyanogen halide-activated polysaccharide is used) or at 30° to 100° C at pH 9 to 14 (if epihalohydrin-activated polysaccharide is used) in an aqueous solvent (e.g., water). The reaction of polysaccharide with the alkyl glycidyl ether or phenyl glycidyl ether [Reactions 30 and 31] may be carried out at 30° to 100° C in a suitable solvent such as water or an aqueous alkanol (e.g., aqueous methanol or aqueous ethanol). The physical adsorption of tannin on the water-insoluble, hydrophilic carrier is readily performed by contacting tannin with said carrier in an aqueous solvent (e.g., water). For example, the physical adsorption is carried out by adding the carrier to an aqueous tannin solution and then allowing the mixture to stand at a temperature of about 0° to 50° at a pH of 3 to 10. The preferred concentration of tannin in the solution may be about 0.5 to about 1.0 w/v%. After the above-mentioned treatment, the water-insoluble tannin preparation may be recovered by filtration or centrifugation.

USES OF THE INVENTION

The water-insoluble tannin preparation of the present invention has a specific and unique affinity for proteins and can be used for immobilization or insolubilization of enzymes. That is, an immobilized enzyme is prepared by adsorbing the enzyme physically on the water-insoluble tannin preparation. All of catalytically active enzymes are preferably used for this purpose. For example, enzymes which may be employed to produce immobilized preparations thereof include oxidoreductases such as amino acid oxidase, catalase, xanthin oxidase, glucose oxidase, glucose-6-phosphate dehydrogenase, glutamate dehydrogenase, cytochrome C oxidase, tyrosinase, lactate dehydrogenase, peroxidase, 6-phosphogluconate dehydrogenase and malate dehydrogenase; transferases such as aspartate acetyltransferase, aspartate aminotransferase, glycine aminotransferase, glutamic oxalacetic aminotransferase, glutamic pyruvic aminotransferase, creatine phosphokinase, histamine methyltransferase, pyruvate kinase, fructokinase, hexokinase ε-lysine actyltransferase and leucine aminopeptidase; hydrolases such as asparaginase, acetylcholinesterase, aminoacylase, amylase, arginase, L-arginine deiminase, invertase, urease, uricase, esterase, β-galactosidase, kallikrein, chymotrypsin, trypsin, thrombin, naringinase, nucleotidase, papain, hyaluronidase, plasimin, pectinase, hesperidinase, pepsin, penicillinase, penicillin amidase, phospholipase, phosphatase, lactase, lipase, ribonuclease and renin; lyases such as aspartate decarboxylase, aspartase, citrate lyase, glutamate decarboxylase, histidine ammonia-lyase, phenylalanine ammonialyase, fumarase, fumarate hydratase and malate synthetase; isomerases such as alanine racemase, glucose isomerase, glucosephosphate isomerase, glutamate racemase, lactate racemase and methionine racemase and lygases such as asparagine synthetase.

The above-mentioned enzymes are not necessarily in pure forms, but crude enzyme solutions may be per se employed in the immobilization step. For example, the extracts of animal or plant tissues and the cell-free extracts of microorganisms may be preferably used as the enzyme solution. These extracts may of course be partially purified prior to using in the present invention. Moreover, the immobilization may be performed by using a mixture of two or more enzymes mentioned above. The physical adsorption of the enzyme to the water-insoluble tannin preparation (i.e., the immobilization of the enzyme) can be accomplished by contacting said enzyme with the water-insoluble tannin preparation in an aqueous solvent. For example, the enzyme is dissolved in water, the water-insoluble tannin preparation is suspended in the enzyme solution, and the suspension is stirred. By this operation the enzyme is adsorbed specifically on the tannin preparation, and other compounds such as RNA, DNA, saccharides and low molecular compounds remain dissolved in the suspension. After the operation, the immobilized enzyme of the invention can be readily obtained by filtering or centrifuging the suspension to collect the precipitates, followed by washing the precipitates with a suitable buffer solution and/or water.

Alternatively, the physical adsorption of the enzyme on the water-insoluble tannin preparation may be conducted by a column method. For example, the water-insoluble tannin preparation is charged into a column. By passing an enzyme solution through the column at a suitable flow rate (e.g., at a space velocity of 0.1 to 100 $hr^{-1}$), the enzyme is adsorbed specifically on the column of the tannin preparation and the other compounds are eluted into the effluent. After this treatment, an immobilized enzyme of the present invention is easily obtained by washing the column with a suitable buffer solution and/or water. The above-mentioned physical adsorption of enzymes on the water-insoluble tannin preparation is preferably carried out at a temperature of 0° to 70° C and at a pH of 2 to 12 in an aqueous solution.

When aminoacylase is employed, the enzymatic activity of an immobilized aminoacylase preparation may be increased by carrying out the above-mentioned treatment in the presence of an alkanol (e.g., butanol), acetone or a hydrophobic solvent (e.g., ethylene glycol). In any event, the immobilized enzyme of the present invention (i.e., the enzyme physically adsorbed on the water-insoluble tannin preparation) obtained by the above-mentioned method retains a high level of enzymatic activity for a long period of time and is useful as a heterogeneous catalyst to induce various enzymatic reactions. Moreover, since the water-insoluble tannin preparation binds the enzyme very firmly, the immobilized enzyme can be used repeatedly for the enzymatic reaction with substrates and no substantial desorption of the bound enzyme is brought about during the enzymatic reaction or even by addition of substrates in a high concentration.

Additionally, when the activity of the immobilized enzyme is decreased by repeated use thereof, its activity can be restored by treating it with a solution containing 0.01 to 1.0 N-hydrochloric acid, 0.01 to 0.1 N-sodium hydroxide, a surfactant or ethylene glycol; washing with water and then contacting it again with the enzyme solution.

As previously mentioned, the water-insoluble tannin preparation does not adsorb amino acids, organic acids, sugars, nucleic acids and high molecular compounds other than proteins, but it shows strong ability to bind proteins specifically and reversibly. By making use of these characteristics, the water-insoluble tannin preparation of the invention can be used as an adsorbent in separating or isolating proteins from crude protein solutions, or purifying the isolated proteins.

For example, proteins can be separated from a crude protein solution by contacting the solution with the water-insoluble tannin preparation (whereby the proteins are adsorbed by the tannin preparation), collecting the tannin preparation, and then eluting the proteins therefrom. Enzymes, albumin, globulin, hormonal proteins and other therapeutically or industrially valuable proteins may be readily recovered by these operations. Extracts of animal or plant tissues, fermentation broths or cell-free extracts of microorganisms, animal or plant secretions and/or any other protein solutions may be employed for the separation of proteins, provided only that the proteins are soluble in said solutions.

Proteins may be adsorbed by the water-insoluble tannin preparation by adding the tannin preparation to the crude protein solution, and stirring the mixture for a period of about one to about 24 hours. It is preferred to carry out said adsorption step at 0° to 60° C and at a pH of about 2 to about 12. It is also preferred to use a crude protein solution having a specific electric conductivity of 0 to about 400 m mho. After the adsorption step, the water-insoluble tannin preparation having proteins adsorpted thereto can be easily collected by filtration or centrifugation and, by eluting said tannin preparation with a suitable solvent, the desired proteins can be recovered in high purity. Strong acid solutions (e.g. 0.01 to 1 N hydrochloric acid), strong alkali solutions (e.g. 0.01 to 1 N sodium hydroxide), aqueous surfactant solutions, aqueous 3 to 6 M urea solution, ethanol and n-butanol are suitable as the eluting solvent. When the adsorbed proteins are enzymes, a solution containing enzyme inhibitors may also be used as the eluting solvent.

The above-mentioned adsorption and elution steps may be carried out by the column method. For example, the water-insoluble tannin preparation is charged into a column. After the column is washed with water and/or a buffer solution, a protein solution (pH 3 to 10) is passed through the column at a suitable flow rate (e.g., at a space velocity of 0.01 to 100 $hr^{-1}$). By this operation, proteins contained in the solution are adsorbed by the tannin preparation and the other compounds pass into the effluent. The adsorbed proteins may be eluted from the column by treating said column with an eluting solvent mentioned above. The adsorption and elution steps of the present invention can be performed without denaturation of the proteins and, by treating crude enzyme solutions according to this process, enzymes with a high biological activity can be obtained without contamination with amino acids, organic acids, nucleic acids and high molecular weight compounds other than the proteins.

Alcoholic beverages such as "Japanese sake" (a fermented liquor made from rice), beer, wine; liquid seasonings such as vinegar or soy sauce; and fruit juices such as orange, apple or grape juice are usually contaminated with proteins due to the raw materials employed or microorganisms used in the fermentation or brewing steps. The presence of proteins detracts from the quality of these liquid products. Moreover, due to such protein contaminants, these liquid products become turbid during storage. Prior to being placed on the market, therefore, these products must be further processed to prevent sedimentation of proteins. The water-insoluble tannin preparation of the invention can be used as an adsorbent in removing proteins from these liquid products.

For example, proteins contained in these products are removed by simply contacting them with the water-insoluble tannin preparation which adsorbs the proteins, and then filtering or centrifuging the mixture to separate the tannin preparation. Since the water-insoluble tannin preparation does not adsorb amino acids, nucleic acids and other compounds which affect the taste, flavor and/or color, it is especially suitable for removing protein contaminants from these liquid products without adversely altering the quality thereof. Concomitantly, when medicines or chemical reagents are contaminated with proteins, they may be purified in the same manner. Also, since the tannin preparation of the invention is stable enough so as to prevent any leakage of tannin during the adsorption step, various solutions (e.g., alcoholic beverages, liquid seasonings, fruit juices and aqueous solutions of medicines or chemical reagents) purified with said preparation are in no way contaminated with tannin.

Further, after the water-insoluble tannin preparation having proteins adsorbed thereto is separated from the liquid product, the adsorbed proteins may be liberated from the tannin preparation by treating it with an eluting solvent such as 0.01 to 1 N hydrochloric acid, 0.01 to 1 N sodium hydroxide, an aqueous surfactant solution, an aqueous 3 to 6 M urea solution, ethanol or n-butanol. The tannin preparation thus recovered may be used repeatedly for the same purposes mentioned above.

The water-insoluble tannin preparation can also be used for stopping an enzymatic reaction. For example, after an enzyme is reacted with a substrate for a sufficient period of time, the reaction may be stopped by adding the tannin preparation to the mixture of enzyme and substrate, thereby adsorbing the enzyme thereon, and then filtering or centrifuging the mixture to remove the tannin preparation and the enzyme. According to this method, even substrates and reaction products which are unstable to heating or at acidic or alkaline conditions may be recovered from the reaction mixture, without decomposition, because the stoppage of the enzymatic reaction and the removal of enzymes therefrom are carried out without heating or acidifying the mixture or making it alkaline.

Practical and presently preferred embodiments of the present invention are show in the following Examples. Throughout the Examples, the amount of protein is estimated by the Copper-Folin Method described in the "Journal of Biological Chemistry," 193, 265 (1951).

EXAMPLE 1

(1) 4 g of cellulose powder (manufactured by Toyo Roshi Co., under the trade name "Cellulose Powder C") are immersed in 40 ml of an aqueous 25% sodium hydroxide solution. 10 ml of epichlorohydrin are added to the suspension, and the mixture is stirred vigorously at 60° C for 30 minutes. After the reaction, the epichlorohydrin-activated cellulose thus obtained is collected by filtration, washed with water and then suspended in 80 ml of an aqueous solution (pH 10) containing hexamethylenediamine (hexamethylenediamine content: 2.2 g/80 ml). The suspension is stirred slowly at 60° C for 2 hours. The precipitates are collected by filtration and washed first with an aqueous 0.1 M sodium bicarbonate solution and then with water. 10.5 g (wet form) of aminohexylcellulose are obtained.

(2) 10.5 g of chinese gallotannin are dissolved in 240 ml of water. The solution is adjusted to pH 10, and 0.3 ml of epichlorohydrin are added thereto. The mixture is stirred at 30° C for 2 hours, whereby an epichlorohydrin-activated chinese gallotannin solution is obtained. The 10.5 g of aminohexyl-cellulose obtained in paragraph (1) are added to the epichlorohydrin-activated chinese gallotannin solution, and the mixture is stirred at 45° C for 6 hours. After the reaction, the precipitates are collected by filtration and washed first with an aqueous 0.1 M sodium bicarbonate solution and then with water. 11.3 g (wet form) of a water-insoluble tannin preparation [i.e. chinese gallotannin covalently bound to cellulose through the linkage —CH$_2$—CH(OH)— CH$_2$NH—(CH$_2$)$_6$—NHCH$_2$CH(OH)CH$_2$—] are thereby obtained.

(3) 200 mg of aminoacylase (total activity: 4,000 $\mu$ moles/hr) obtained from Aspergillus orizae are dissolved in 6 ml of an aqueous 0.2 M sodium chloride solution (pH 8.0) containing 0.2 v/v% of n-butanol. 500 mg (wet form) of the water-insoluble tannin preparation obtained in paragraph (2) are added to the aminoacylase solution, and the mixture is stirred at 37° C for 30 minutes. The precipitates are then collected by filtration and washed with water. 530 mg (wet form) of an immobilized aminoacylase preparation [i.e., aminoacylase adsorbed by the water-insoluble tannin preparation] are obtained. It shows an aminoacylase activity of 9,376 $\mu$ moles per hour per 10 g (wet form) of the water-insoluble tannin preparation. [Aminoacylase activity is indicated in terms of micromoles of L-methionine which is produced by reaction with N-acetyl-DL-methionine at 37° C at pH 7.0.]

EXAMPLE 2

(1) 10.5 g (wet form) of aminohexyl-cellulose are prepared from 4 g of cellulose powder in the same manner as described in Example 1. The aminohexyl-cellulose is suspended in 100 ml of an aqueous 1 N sodium hydroxide solution. 6 ml of epichlorohydrin are added to the suspension, and the mixture is stirred at 60° C for 30 minutes. The epichlorohydrin-activated aminohexyl-cellulose thus obtained is collected by filtration and washed with water. A solution (pH 10) of 5.2 g of chinese gallotannin in 100 ml of water is added to the epichlorohydrin-activated aminohexyl-cellulose, and the mixture is stirred at 45° C for 6 hours. After the reaction, the precipitates are collected by filtration and washed first with an aqueous 0.1 M sodium carbonate solution and then with water. 11.4 g (wet form) of a water-insoluble tannin preparation [i.e., chinese gallotannin covalently bound to cellulose through the linkage —$CH_2CH(OH)CH_2NH$—$(CH_2)_6$— $NHCH_2$—$CH(OH)CH_2$—] are thereby obtained.

(2) 500 mg (wet form) of the water-insoluble tannin preparation obtained in paragraph (1) and 200 mg of aminoacylase are treated in the same manner as described in Example 1-(3). 525 mg of an immobilized aminoacylase preparation are obtained. It shows an aminoacylase activity of 8,900 $\mu$ moles per hour per 10 g (wet form) of the water-insoluble tannin preparation.

EXAMPLE 3

(1) 4 g of cellulose powder are immersed in 40 ml of an aqueous 25% sodium hydroxide solution at 25° C for 30 minutes, and then washed with water. 10 g of the wet cellulose are suspended in 100 ml of an aqueous 0.1 M sodium bicarbonate solution. The suspension is adjusted to pH 11.5, and 0.4 g of cyanogen bromide is added thereto. The mixture is then stirred at 20° to 25° C for about 8 minutes. During the reaction, the pH is maintained at 11 to 11.5 by the use of an aqueous 5 N-sodium hydroxide solution. After the reaction, the precipitates are collected by filtration and washed first with an aqueous 0.1 M sodium bicarbonate solution cooled to about 4° C and then with cool water. Cyanogen bromide-activated cellulose is obtained thereby.

(2) 5.2 g of chinese gallotannin are dissolved in 100 ml of water. The solution is adjusted to pH 11.5, 0.2 g of cyanogen bromide are added thereto at 20° C, and the mixture is stirred at the same temperature for 8 minutes. During the reaction, the mixture is kept at a pH of 11 to 11.5. The cyanogen bromide-activated chinese gallotannin solution thus obtained is adjusted to pH 10, and a solution (pH 10) of 2.3 g of hexamethylenediamine in 30 ml of water is added thereto. Then, the mixture is stirred at 25° C for 2 hours, whereby an aminohexyl-chinese gallotannin solution is obtained. The cyanogen bromide-activated cellulose obtained in paragraph (1) is added to the aminohexyl-chinese gallotannin solution, and the mixture is stirred at 25° C for 20 hours. After the reaction, the precipitates are collected by filtration and washed first with an aqueous 0.1 M sodium bicarbonate solution and then with water. 11.4 g (wet form) of a water-insoluble tannin preparation [i.e., chinese gallotannin covalently bound to cellulose through the linkage —$CONH$—$(CH_2)_6$— $NHCO$—] are thereby obtained.

(3) 500 mg (wet form) of the water-insoluble tannin preparation obtained in paragraph (2) and 200 mg of aminoacylase are treated in the same manner as described in Example 1-(3). 530 mg (wet form) of an immobilized aminoacylase preparation are obtained. It shows an aminoacylase activity of 10,600 $\mu$ moles per hour per 10 g (wet form) of the water-insoluble tannin preparation.

EXAMPLE 4

(1) 4 g of cellulose powder and 0.4 g of cyanogen bromide are treated in the same manner as described in Example 3-(1). The cyanogen bromide-activated cellulose thus obtained is suspended in 100 ml of an aqueous solution (pH 10) containing hexamethylenediamine (hexamethylenediamine content: 2.3 g/100 ml). The suspension is stirred at 25° C for 2 hours. After the reaction, the precipitates are collected by filtration and washed first with an aqueous 0.1 M sodium bicarbonate solution and then with water. 10.6 g (wet form) of aminohexyl-cellulose are thereby obtained.

(2) 5.2 g of chinese gallotannin and 0.2 g of cyanogen bromide are treated in the same manner as described in Example 3-(2). The cyanogen bromide-activated chinese gallotannin solution thus obtained is adjusted to pH 10 with 5 N hydrochloric acid, and a solution (pH 10) of 2.0 g of $\epsilon$-aminocaproic acid in 30 ml of water is added thereto. Then, the mixture is stirred at 25° C for 2 hors, whereby a carboxypentyl-chinese gallotannin solution is obtained. 10.6 g (wet form) of the aminohexyl-cellulose obtained in paragraph (1) are suspended in the carboxypentyl-chinese gallotannin solution, and the suspension is adjusted to pH 4.8. 4 ml of an aqueous 20% 1-ethyl-3-(3-dimethylaminopropyl)-carbodiimide solution are added dropwise to the suspension over a period of 5 minutes. During the addition, the suspension is kept at a pH of about 4.8 with 0.5 N hydrochloric acid. The suspension is then stirred at 28° C for 20 hours. After the reaction, the precipitates are collected by filtration and washed first with an aqueous 0.1 M sodium bicarbonate solution and then with water. 11.5 g (wet form) of a water-insoluble tannin preparation [i.e., chinese gallotannin covalently bound to cellulose through the linkage —$CONH$—$(CH_2)_5$—$CONH$—$(CH_2)_6$— $NHCO$—] are thereby obtained.

(3) 500 mg (wet form) of the water-insoluble tannin preparation obtained in paragraph (2) and 200 mg of aminoacylase are treated in the same manner as described in Example 1-(3). 530 mg (wet form) of an immobilized aminoacylase preparation are obtained. It shows the aminoacylase activity of 7,400 $\mu$ moles per hour per 10 g (wet form) of the water-insoluble tannin preparation.

EXAMPLE 5

(1) 10.5 g (wet form) of aminohexyl-cellulose are prepared from 4 g of cellulose powder in the same manner as described in Example 1-(1).

(2) 5.2 g of chinese gallotannin and 0.2 g of cyanogen bromide are treated in the same manner as described in Example 3-(2). The cyanogen bromide-activated chinese gallotannin solution thus obtained is adjusted to pH 10 with 5 N hydrochloric acid, and a solution (pH 10) of 3.1 g of ethylenediamine in 30 ml of water is added thereto. Then, the mixture is stirred at 25° C for 2 hours. 0.2 ml of epichlorohydrin are added to the mixture, and said mixture is further stirred at 25° C for 2 hours, whereby an epichlorohydrin-activated aminoethyl-chinese gallotannin solution is obtained. 10.5 (wet form) of the aminohexyl-cellulose obtained in paragraph (1) are added to the epichlorohydrin-activated aminoethyl-chinese gallotannin solution, and the mixture is stirred at 45° C for 2 hours. After the reaction, the precipitates are collected by filtration and washed first with an aqueous 0.1 M sodium bicarbonate solution and then with water. 11.1 g (wet form) of a water-insoluble tannin preparation [i.e., chinese gallotannin covalently bound to cellulose through the linkage —$CONHCH_2CH_2NHCH_2CH(OH)CH_2NH$—$(CH_2)_6$—$NHCH_2$— $CH(OH)CH_2$—] are thereby obtained.

(3) 500 mg (wet form) of the water-insoluble tannin preparation obtained in paragraph (2) and 200 mg of aminoacylase are treated in the same manner as described in Example 1-(3). 505 mg (wet form) of an immobilized aminoacylase preparation are obtained. It shows the aminoacylase activity of 2,900 $\mu$ moles per hour per 10 g (wet form) of the water-insoluble tannin preparation.

EXAMPLE 6

(1) 10.6 g (wet form) of aminohexyl-cellulose are prepared from 4 g of cellulose powder in the same manner as described in Example 4-(1).

(2) 5.2 g of chinese gallotannin are dissolved in 100 ml of water. The solution is adjusted to pH 11.5, and 0.2 g of cyanogen bromide are added thereto. The mixture is stirred at 20° to 25° C for about 8 minutes. During the reaction, the mixture is kept at a pH of 11 to 11.5 with 5 N sodium hydroxide solution. The cyanogen bromide-activated chinese gallotannin solution thus obtained is adjusted to pH 11.0. 10.6 g (wet form) of the aminohexyl-cellulose obtained in paragraph (1) are suspended in the cyanogen bromide-activated chinese gallotannin solution, and the suspension is stirred slowly at 40° C for 2 hours. After the reaction, the precipitates are collected by filtration and washed first with an aqueous 0.1 M sodium bicarbonate solution and then with water. 11.6 g (wet form) of a water-insoluble tannin preparation [i.e., chinese gallotannin covalently bound to cellulose through the linkage $-CONH-(CH_2)_6-NHCO-$] are thereby obtained.

(3) 500 mg (wet form) of the water-insoluble tannin preparation obtained in paragraph (2) and 200 mg of aminoacylase are treated in the same manner as described in Example 1-(3). 530 mg (wet form) of an immobilized aminoacylase preparation are obtained. It shows an aminoacylase activity of 11,000 $\mu$ moles per hour per 10 g (wet form) of the water-insoluble tannin preparation.

EXAMPLE 7

(1) 10.5 g (wet form) of a water-insoluble tannin preparation [i.e., nutgalls-tannin covalently bound to cellulose through the linkage $-CONH-(CH_2)_6-NHCO-$] are prepared from 5 g of nutgalls-tannin in the same manner as described in Example 6-(2).

(2) 500 mg (wet form) of a water-insoluble tannin preparation obtained in paragraph (1) and 200 mg of aminoacylase are treated in the same manner as described in Example 1-(3). 525 mg (wet form) of an immobilized aminoacylase preparation are obtained. It shows the aminoacylase activity of 9,800 $\mu$ moles per hour per 10 g (wet form) of the water-insoluble tannin preparation.

EXAMPLE 8

(1) 10.9 g (wet form) of a water-insoluble tannin preparation [i.e., persimmon tannin covalently bound to cellulose through the linkage $-CONH-(CH_2)_6-NHCO-$] are prepared from 100 ml of persimmon tannin in the same manner as described in Example 6-(2).

(2) 500 mg (wet form) of the water-insoluble tannin preparation obtained in paragraph (1) and 200 mg of aminoacylase are treated in the same manner as described in Example 1-(3). 520 mg (wet form) of an immobilized aminoacylase preparation are obtained. It shows the aminoacylase activity of 7,600 $\mu$ moles per hour per 10 g (wet form) of the water-insoluble tannin preparation.

EXAMPLE 9

(1) 10.5 g (wet form) of a water-insoluble tannin preparation [i.e., catechol tannin covalently bound to cellulose through the linkage $-CONH-(CH_2)_6-NHCO-$] are prepared from 3 g of catechol tannin in the same manner as described in Example 6-(2).

(2) 500 mg (wet form) of the water-insoluble tannin preparation obtained in paragraph (1) and 200 mg of aminoacylase are treated in the same manner as described in Example 1-(3). 510 mg (wet form) of an immobilized aminoacylase preparation are obtained. It shows the aminoacylase activity of 2,100 $\mu$ moles per hour per 10 g (wet form) of the water-insoluble tannin preparation.

EXAMPLE 10

(1) An aminohexyl-chinese gallotannin solution is prepared from 5.2 g of chinese gallotannin in the same manner as described in Example 3-(2). 0.3 ml of epichlorohydrin are added to the solution. Then, the mixture is stirred at 30° C for 2 hours, whereby an epichlorohydrin-activated aminohexyl-chinese gallotannin solution is obtained. 10 g of cellulose [pre-treated with a sodium hydroxide solution in the same manner as described in Example 1-(1)] are added to the epichlorohydrin-activated aminohexyl-chinese gallotannin solution, and the mixture is stirred at 45° C for 20 hours. After the reaction, precipitates are collected by filtration and washed first with an aqueous 0.1 M sodium bicarbonate solution and then with water. 11.0 g (wet form) of a water-insoluble tannin preparation [i.e., chinese gallotannin covalently bound to cellulose through the linkage $-CONH-(CH_2)_6-NHCH_2CH(OH)CH_2-$] are thereby obtained.

(2) 500 mg (wet form) of the water-insoluble tannin preparation obtained in paragraph (1) and 200 mg of aminoacylase are treated in the same manner as described in Example 1-(3). 510 mg (wet form) of an immobilized aminoacylase preparation are obtained. It shows the aminoacylase activity of 1,200 $\mu$ moles per hour per 10 g (wet form) of the water-insoluble tannin preparation.

EXAMPLE 11

(1) Epichlorohydrin-activated cellulose is prepared from 4 g of cellulose powder in the same manner as described in Example 1-(1). The epichlorohydrin-activated cellulose is suspended in 80 ml of an aqueous solution (pH 10) containing 2-aminoethanol (2-aminoethanol content: 3.1 g/80 ml). The suspension is stirred at 60° C for 20 hours. After the reaction, the precipitates are collected by filtration and washed first with an aqueous 0.1 M sodium bicarbonate solution and then with water. 10.4 g (wet form) of aminoethyl-cellulose are thereby obtained.

(2) 10.5 g of chinese gallotannin are dissolved in 240 ml of water. The solution is adjusted to pH 10, and 0.3 ml of epichlorohydrin are added thereto. Then, the mixture is stirred at 30° C for 2 hours, whereby an epichlorohydrin-activated chinese gallotannin solution is obtained. 10.4 g (wet form) of the aminoethyl-cellulose obtained in paragraph (1) are added to the epichlorohydrin-activated chinese gallotannin solution, and the mixture is stirred at 45° C for 3 hours. After the reaction, the precipitates are collected by filtration and washed first with an aqueous 0.1 M sodium bicarbonate solution and then with water. 11.1 g (wet form) of a water-insoluble tannin preparation [i.e., chinese gallotannin covalently bound to cellulose through the linkage $-CH_2CH-(OH)CH_2NHCH_2CH_2OCH_2CH(OH)CH_2-$] are thereby obtained.

(3) 500 mg (wet form) of the water-insoluble tannin preparation obtained in paragraph (2) and 200 mg of amino-acylase are treated in the same manner as described in Example 1-(3). 520 mg (wet form) of an immobilized aminoacylase preparation are obtained. It shows an aminoacylase activity of 2,410 μ moles per hour per 10 g (wet form) of the water-insoluble tannin preparation.

EXAMPLE 12

(1) Epichlorohydrin-activated cellulose and an aminohexyl-chinese gallotannin solution are prepared from 4 g of cellulose powder and 5.2 g of chinese gallotannin in the same manner as described in Example 1-(1) and Example 3-(2), respectively. The epichlorohydrin-activated cellulose is added to the aminohexyl-chinese gallotannin solution, and the mixture is stirred at 45° C for 4 hours. After the reaction, the precipitates are collected by filtration and washed first with an aqueous 0.1 M sodium bicarbonate solution and then with water. 10.9 g (wet form) of a water-insoluble tannin preparation [i.e., chinese gallotannin covalently bound to cellulose through the linkage $-CONH-(CH_2)_6-NHCH_2CH(OH)CH_2-$] are thereby obtained.

(2) 500 mg (wet form) of the water-insoluble tannin preparation obtained in paragraph (1) and 200 mg of aminoacylase are treated in the same manner as described in Example 1-(3). 530 mg (wet form) of an immobilized aminoacylase preparation are obtained. It shows the aminoacylase of 9,430 μ moles per hour per 10 g (wet form) of the water-insoluble tannin preparation.

EXAMPLE 13

(1) 15 g of 2-hydroxy-3-[4-(2,3-epoxypropyloxy) butyloxy] propyl-agarose (manufactured by Pharmacia Fine Chemicals under the trade designation "Epoxy-activated Sepharose 6B") are washed with 500 ml of water, 500 ml of an aqueous 0.5 M sodium chloride solution and 500 ml of water, in that order. One g of chinese gallotannin dissolved in 100 ml of an aqueous 0.1 M sodium bicarbonate solution is added to the agarose. The mixture is then adjusted to pH 10.5 with an aqueous 8 N sodium hydroxide solution, and shaken at 37° C for 26 hours. After the reaction, the precipitates are collected by filtration and washed first with one liter of water, then with 500 ml of a 0.2 M carbonate buffer solution (pH 10) and finally with one liter of water. 14.9 g (wet form) of a water-insoluble tannin preparation [i.e., chinese gallotannin covalently bound to agarose through the linkage $-CH_2CH(OH)-CH_2O-(CH_2)_4-OCH_2CH(OH)CH_2-$] are thereby obtained.

(2) 500 mg (wet form) of the water-insoluble tannin preparation obtained in paragraph (1) and 200 mg of aminoacylase are treated in the same manner as described in Example 1-(3). 490 mg (wet form) of an immobilized aminoacylase preparation are obtained. It shows an aminoacylase activity of 800 μ moles per hour per 10 g (wet form) of the water-insoluble tannin preparation.

EXAMPLE 14

(1) 4 g of agarose (manufactured by Pharmacia Fine Chemicals under the trade designation "Sepharose 4B") are washed with 500 ml of water, 500 ml of an aqueous 0.5 M sodium chloride solution and 500 ml of water, successively. The agarose is suspended in 500 ml of an aqueous 0.1 M sodium bicarbonate solution and the pH is adjusted to 11.5. 0.4 g of cyanogen bromide are added to the suspension, and the mixture is stirred at 20° to 25° C for about 8 minutes. During the reaction, the mixture is kept at a pH of 11 to 11.5. Then, the precipitates are collected by filtration and washed first with one liter of an aqueous 0.1 M sodium bicarbonate at about 4° C and then with one liter of cool water. Cyanogen bromide-activated agarose is thereby obtained.

(2) 5.2 g of chinese gallotannin are dissolved in 100 ml of water, and adjusted to pH 11.5. 0.2 g of cyanogen bromide are added to the solution at 20° C, and the mixture is stirred at the same temperature for 8 minutes. During the reaction, the mixture is kept at a pH of 11 to 11.5. The reaction mixture is adjusted to pH 10 with 5 N hydrochloric acid. A solution (pH 10) of 2.3 g of hexamethylenediamine in 30 ml of water is added to the reaction mixture, and said mixture is further stirred at 25° C for 2 hours, whereby an aminohexyl-chinese gallotannin solution is obtained. The cyanogen bromide-activated agarose obtained in paragraph (1) is added to the aminohexyl-chinese gallotannin solution, and the mixture is stirred at 25° C for 2 hours. After the reaction, the precipitates are collected by filtration and washed first with an aqueous 0.1 M sodium bicarbonate solution and then with water. 3.6 g (dry form) of a water-insoluble tannin preparation [i.e., chinese gallotannin covalently bound to agarose through the linkage $-CONH-(CH_2)_6-NHCO-$] are thereby obtained.

(3) 500 mg (wet form) of the water-insoluble tannin preparation obtained in paragraph (2) and 200 mg of aminoacylase are treated in the same manner as described in Example 1-(3). 480 mg (wet form) of an immobilized aminoacylase preparation are obtained. It shows an aminoacylase activity of 2,600 μ moles per hour per 10 g (wet form) of the water-insoluble tannin preparation.

EXAMPLE 15

(1) 4.5 g (dry form) of a water-insoluble tannin preparation [i.e., chinese gallotannin covalently bound to divinylsulfone-cross-linked-dextran through the linkage $-CONH-(CH_2)_6-NHCO-$] are prepared from 4 g of divinylsulfone-cross linked-dextran (manufactured by Pharmacia Fine Chemicals under the trade designation "Sephadex G-100") in the same manner as described in Example 14-(2).

(2) 500 mg (wet form) of the water-insoluble tannin preparation obtained in paragraph (1) and 200 mg of aminoacylase are treated in the same manner as described in Example 1-(3). 505 mg (wet form) of an immobilized aminoacylase preparation are obtained. It shows an aminoacylase activity of 1,720 μ moles per hour per 10 g (wet form) of the water-insoluble tannin preparation.

EXAMPLE 16

(1) 1.3 g of chinese gallotannin are dissolved in 50 ml of water. The solution is adjusted to pH 11.5 with an aqueous 5 N sodium hydroxide solution, and 200 mg of cyanogen bromide are added thereto. The mixture is stirred at 25° C for about 8 minutes. During the reaction, the mixture is kept at a pH of 11 to 11.5. The cyanogen bromide-activated chinese gallotannin solution thus obtained is added to one g of aminohexyl-agarose (manufactured by Pharmacia Fine Chemicals under the trade designation "AH-Sepharose 4B") which has been previously washed with 500 ml of water, 500 ml of an aqueous 0.5 M sodium chloride solution and 500 ml of water, successively. The mixture is stirred at 30° C for 16 hours. After the reaction, the precipitates are collected by filtration and washed first with an aqueous 0.1

M sodium bicarbonate solution and then with water. 1.1 g (dry form) of a water-insoluble tannin preparation [i.e., chinese gallotannin covalently bound to agarose through the linkage —CONH—(CH$_2$)$_6$—NHCO—] are thereby obtained.

(2) 500 mg (wet form) of the water-insoluble tannin preparation obtained in paragraph (1) and 200 mg of aminoacylase are treated in the same manner as described in Example 1-(3). 510 mg (wet form) of an immobilized aminoacylase preparation are obtained. It shows an aminoacylase activity of 2,270 μ moles per hour per 10 g (wet form) of the water-insoluble tannin preparation.

EXAMPLE 17

(1) 3.6 g (wet form) of a water-insoluble tannin preparation [i.e., chinese gallotannin covalently bound to cellulose through the linkage —CONH—(CH$_2$)$_6$—NH-COCH$_2$—] are prepared from 1.3 g of chinese gallotannin and one g of aminohexyl-cellulose (manufactured by Merck Co. under the trade designation "AH-Cellulose") in the same manner as described in Example 16-(1).

EXAMPLE 18

(1) 2 g of p-aminobenzyl-cellulose (manufactured by Seravac Co. under the trade designation "PAB-Cellulose") are washed with 500 ml of water and then suspended in 50 ml of 2 N hydrochloric acid cooled to about 4° C. 10 ml of an aqueous 14% sodium nitrite solution cooled to about 4° C are added dropwise to the suspension for 5 minutes under stirring. The suspension is further stirred at 0° C for one hour. The diazotized p-aminobenzyl-cellulose thus obtained is collected by filtration and washed first with 100 ml of an aqueous 1% sulfamic acid solution cooled to about 4° C and then with 300 ml of cool water. A solution of 1.3 g of chinese gallotannin in 40 ml of a 0.1 M carbonate buffer solution (pH 10) is added to the diazotized p-aminobenzyl-cellulose. Then, the mixture is adjusted to pH 9.2 with an aqueous 8 N sodium hydroxide solution and shaken at 25° C for 20 minutes. After the reaction, the precipitates are collected by filtration and washed first with a 0.1 M carbonate buffer solution (pH 10) and then with water. 4.7 g (wet form) of a water-insoluble tannin preparation [i.e., chinese gallotannin covalently bound to cellulose through the linkage

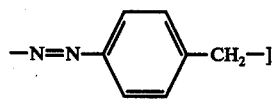

are thereby obtained.

(2) 500 mg (wet form) of the water-insoluble tannin preparation obtained in paragraph (1) and 200 mg of aminoacylase are treated in the same manner as described in Example 1-(3). 520 mg (wet form) of an immobilized aminoacylase preparation are obtained. It shows an aminoacylase activity of 540 μ moles per hour per 10 g (wet form) of the water-insoluble tannin preparation.

EXAMPLE 19

(1) 4.9 mg (wet form) of a water-insoluble tannin preparation [i.e., chinese gallotannin covalently bound to cellulose through the linkage

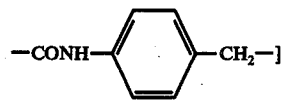

are prepared from 1.3 g of chinese gallotannin and 2 g of p-aminobenzyl-cellulose in the same manner as described in Example 16-(1).

(2) 500 mg (wet form) of the water-insoluble tannin preparation obtained in paragraph (1) and 200 mg of aminoacylase are treated in the same manner as described in Example 1-(3). 520 mg (wet form) of an immobilized aminoacylase preparation are obtained. It shows an aminoacylase activity of 610 μ moles per hour per 10 g (wet form) of the water-insoluble tannin preparation.

EXAMPLE 20

(1) One g of p-aminobenzyl-cellulose is washed with water and then suspended in 25 ml of 2 N hydrochloric acid cooled to about 4° C. 5 ml of an aqueous 14% sodium nitrite solution are added dropwise to the suspension at about 4° C under stirring, and the suspension is stirred at 5° C for one hour. The diazotized p-aminobenzyl-cellulose thus obtained is collected by filtration and washed first with an aqueous 0.1 M sodium bicarbonate solution and then with water. The diazotized p-aminobenzyl-cellulose is suspended in 30 ml of a 0.1 M borate buffer solution (pH 8.0), and 500 mg of hexamethylenediamine are added thereto. Then, the diazotized p-aminobenzyl-cellulose suspension is adjusted to pH 9.5 and stirred at 25° C for 20 hours. The p-aminohexylazobenzyl-cellulose thus obtained is collected by filtration and washed first with an aqueous 0.1 M sodium bicarbonate solution and then with water. A cyanogen bromide-activated chinese gallotannin solution prepared from 0.7 g of chinese gallotannin in the same manner as described in Example 16-(1) is added to the p-aminohexylazobenzyl-cellulose, and the mixture is stirred at 10.5° C for 16 hours. After the reaction, the precipitates are collected by filtration and washed with water. 2.3 g (wet form) of a water-insoluble tannin preparation [i.e. chinese gallotannin covalently bound to cellulose through the linkage

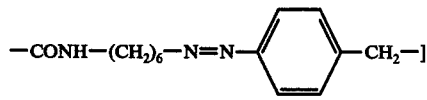

are thereby obtained.

(2) 500 mg (wet form) of the water-insoluble tannin preparation obtained in paragraph (1) and 200 mg of aminoacylase are treated in the same manner as described in Example 1-(3). 530 mg (wet form) of an immobilized aminoacylase preparation are obtained. It shows an aminoacylase activity of 745 μ moles per hour per 10 g (wet form) of the water-insoluble tannin preparation.

EXAMPLE 21

(1) 1.1 g (wet form) of a water-insoluble tannin preparation [i.e. chinese gallotannin covalently bound to porous glass through the linkage

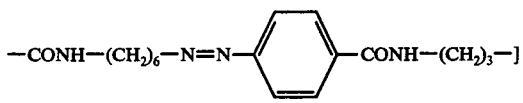

are prepared from one g of p-aminobenzamidopropyl-porous glass (manufactured by Corning Glass Works under the trade designation "Enchol") and 0.7 g of chinese gallotannin in the same manner as described in Example 20-(1).

(2) 500 mg (wet form) of the water-insoluble tannin preparation obtained in paragraph (1) and 200 mg of aminoacylase are treated in the same manner as described in Example 1-(3). 510 mg (wet form) of an immobilized aminoacylase preparation are obtained. It shows an aminoacylase activity of 4,530 $\mu$ moles per hour per 10 g (wet form) of the water-insoluble tannin preparation.

EXAMPLE 22

(1) 500 mg of wool are dispersed in 30 ml of an aqueous 0.1 M phosphate buffer solution (pH 7.0). 500 mg of hexamethylenediamine and 200 mg of 1-ethyl-3-(3-dimethylaminopropyl) carbodiimide are added to the dispersion. Then, the dispersion is adjusted to pH 6.0 and stirred at 25° C for 20 hours. The aminohexyl-wool thus obtained is collected by filtration and washed first with an aqueous 0.1 M sodium bicarbonate solution and then with water, successively. A cyanogen bromide-activated chinese gallotannin solution prepared from 5.2 g of chinese gallotannin in the same manner as described in Example 16-(1) is added to the aminohexyl-wool, and the mixture is stirred at 10° C for 16 hours. After the reaction, the precipitates are collected by filtration and washed first with an aqueous 0.1 M sodium bicarbonate solution and then with water. 530 mg (wet form) of a water-insoluble tannin preparation [i.e. chinese gallotannin covalently bound to wool through the linkage —CONH—(CH$_2$)$_6$NH—] are thereby obtained.

(2) 500 mg (wet form) of the water-insoluble tannin preparation obtained in paragraph (1) and 200 mg of aminoacylase are treated in the same manner as described in Example 1-(3). 510 mg (wet form) of an immobilized aminoacylase prepartion are obtained. It shows an aminoacylase activity of 420 $\mu$ moles per hour per 10 g (wet form) of the water-insoluble tannin preparation.

EXAMPLE 23

(1) 530 mg (wet form) of a water-insoluble tannin preparation [i.e. chinese gallotannin covalently bound to polyacrylamide cross-linked with N,N'-methylenebisacrylamide through the linkage —CONH—(CH$_2$)$_6$—NHCOCH$_2$—] are prepared from 500 mg of carboxymethyl-polyacrylamide cross linked with N,N'-methylenebisacrylamide (manufactured by Bio-Rad Co. under the trade designation "Bio-Gel CM-2") and 0.6 g of chinese gallotannin in the same manner as described in Example 22-(1).

(2) 500 mg (wet form) of the water-insoluble tannin preparation obtained in paragraph (1) and 200 mg of aminoacylase are treated in the same manner as described in Example 1-(3). 520 mg (wet form) of an immobilized aminoacylase preparation are obtained. It shows an aminoacylase activity of 1,920 $\mu$ moles per hour per 10 g (wet form) of the water-insoluble tannin preparation.

EXAMPLE 24

(1) 505 mg (wet form) of a water-insoluble tannin preparation [i.e. chinese gallotannin covalently bound to polymethacrylic acid cross-linked with divinylbenzene through the linkage —CONH—(CH$_2$)$_6$—NH—] are prepared from 500 mg of polymethyacrylic acid cross-linked with divinylbenzene (manufactured by Rohm & Haas Co. under the trade designation "Amberlite IRC-50") and 0.6 g of chinese gallotannin in the same manner as described in Example 22-(1).

(2) 500 mg (wet form) of the water-insoluble tannin preparation obtained in paragraph (1) and 200 mg of aminoacylase are treated in the same manner as described in Example 1-(3). 510 mg (wet form) of an immobilized aminoacylase preparation are obtained. It shows an aminoacylase activity of 1,010 $\mu$ moles per hour per 10 g (wet form) of the water-insoluble tannin preparation.

EXAMPLE 25

(1) One g of chitosan (manufactured by Kyowa Yushi Kogyo Co. under the trade designation "Fronac N") is suspended in 30 ml of an aqueous 0.1 N sodium hydroxide solution, and 0.5 ml of epichlorohydrin are added thereto. The mixture is stirred at 30° C for 24 hours. The epichlorohydrin-activated chitosan thus obtained is collected by filtration and washed first with an aqueous 0.1 M sodium carbonate solution and then with water. Then, the epichlorohydrin-activated chitosan is suspended in 30 ml of an aqueous solution containing chinese gallotannin (tannin content: one g/30 ml). The suspension is stirred at 45° C for 16 hours. After the reaction, the precipitates are collected by filtration and washed first with an aqueous 0.1 M sodium carbonate solution and then with water. 1.1 g (wet form) of a water-insoluble tannin preparation [i.e. chinese gallotannin covalently bound to chitosan through the linkage —CH$_2$CH(OH)CH$_2$—] are thereby obtained.

(2) 500 mg (wet form) of the water-insoluble tannin preparation obtained in paragraph (1) and 200 mg of aminoacylase are treated in the same manner as described in Example 1-(3). 510 mg (wet form) of an immobilized aminoacylase preparation are obtained. It shows an aminoacylase activity of 480 $\mu$ moles per hour per 10 g (wet form) of the water-insoluble tannin preparation.

EXAMPLE 26

(1) 1.1 g (dry form) of a water-insoluble tannin preparation [i.e. chinese gallotannin covalently bound to polyacrylamide cross-linked with N,N'-methylenebisacrylamide through the linkage

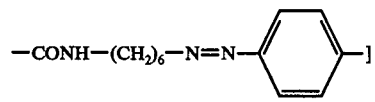

are prepared from one g of p-aminophenyl-polyacrylamide cross-linked with N,N'-methylenebisacrylamide and 0.6 g of chinese gallotannin in the same manner as described in Example 20-(1).

(2) 500 mg (wet form) of the water-insoluble tannin preparation obtained in paragraph (1) and 200 mg of aminoacylase are treated in the same manner as described in Example 1-(3). 520 mg (wet form) of an immobilized aminoacylase preparation are obtained. It shows an aminoacylase activity of 640 μ moles per hour per 10 g (wet form) of the water-insoluble tannin preparation.

EXAMPLE 27

(1) 1.1 g (dry form) of a water-insoluble tannin preparation [i.e. chinese gallotannin covalently bound to polyacrylamide cross-linked with N,N'-methylenebisacrylamide through the linkage —CONH—$(CH_2)_6$—] are prepared from one g of hydrazino-polyacrylamide cross-linked with N,N'-methylenebisacrylamide (manufactured by Koch-Light Labs Ltd. under the trade designation "Enzacryl AH") and 0.6 g of chinese gallotannin in the same manner as described in Example 20-(1).

(2) 500 mg (wet form) of the water-insoluble tannin preparation obtained in paragraph (1) and 200 mg of aminoacylase are treated in the same manner as described in Example 1-(3). 520 mg (wet form) of an immobilized aminoacylase preparation are obtained. It shows an aminoacylase activity of 480 μ moles per hour per 10 g (wet form) of the water-insoluble tannin preparation.

EXAMPLE 28

A water-insoluble tannin preparation [i.e. chinese gallotannin covalently bound to cellulose through the linkage —$CH_2CH(OH)CH_2NH$—$(CH_2)_6$—$NHCH_2CH(OH)CH_2$—] is prepared in the same manner as described in Example 1-(2). 25 mg of glucose isomerase (total activity: 690 units) dissolved in 20 ml of an aqueous 0.1 M sodium chloride solution are added to 500 mg (wet form) of the water-insoluble tannin preparation, and the mixture is stirred at 25° C for 20 minutes. Then, the precipitates are collected by filtration and washed with water. 500 mg (wet form) of an immobilized glucose isomerase preparation [i.e. glucose isomerase adsorbed by the water-insoluble tannin preparation] are thereby obtained. It shows an isomerase activity of 326 units. [One unit of glucose isomerase is defined as the enzymatic activity which affords one mg of fructose by reaction with an aqueous 3.6% glucose solution at 70° C for 1 hour in the presence of 0.025 M magnesium sulfate].

EXAMPLE 29

A water-insoluble tannin preparation [i.e. chinese gallotannin covalently bound to cellulose through the linkage —CONH—$(CH_2)_6$NHCO—] is prepared in the same manner as described in Example 6-(2). 500 mg (wet form) of the water-insoluble tannin preparation and 25 mg of glucose isomerase (total activity: 690 units) are treated in the same manner as described in Example 28. 500 mg (wet form) of an immobilized glucose isomerase preparation [i.e. glucose isomerase adsrobed by the water-insoluble tannin preparation] are thereby obtained. It shows a glucose isomerase activity of 319 units.

EXAMPLE 30

250 mg of papain are added to 100 ml of an aqueous 0.01 M citric acid-potassium phosphate buffer solution (pH 6.2) containing 5 mM of cystein and 1 mM of ethylenediamine tetraacetic acid. The mixture is stirred at room temperature for 30 minutes and then filtered. 500 mg (wet form) of a water-insoluble tannin preparation [i.e. chinese gallotannin covalently bound to cellulose through the linkage —$CH_2CH(OH)$—$CH_2NH$—$(CH_2)_6$—$NHCH_2CH(OH)CH_2$—] prepared in the same manner as described in Example 1-(2) are added to 20 ml of the filtrate (papain activity: 64 units), and the mixture is stirred at 25° C for 30 minutes. Then, the precipitates are collected by filtration and washed with water. 500 mg (wet form) of an immobilized papain preparation [i.e. papain adsorbed on the water-insoluble tannin preparation] are thereby obtained. It shows a papain activity of 20 units. [One unit of papain is defined as the enzymatic activity which decomposes one μ mole of α-benzoyl-arginine ethyl ester by reaction with said arginine ester at pH 6.2 for one minute]

EXAMPLE 31

A water-insoluble tannin preparation [i.e. chinese gallotannin covalently bound to cellulose through the linkage —$CH_2CH(OH)CH_2NH$—$(CH_2)_6$—$NHCH_2CH(OH)CH_2$—] is prepared in the same manner as described in Example 1-(2). 20 ml of an aqueous solution (pH 5.0) of glucose oxidase (total activity: 376 units) obtained from Aspergillus niger, are added to one g (wet form) of the water-insoluble tannin preparation, and the mixture is stirred at 25° C for 30 minutes. Then, the precipitates are collected by filtration and washed with water. 1.1 g (wet form) of an immobilized glucose oxidase preparation [i.e. glucose oxidase adsorbed on the water-insoluble tannin preparation] are thereby obtained. It shows a glucose oxidase activity of 162 units. [One unit of glucose oxidase is defined as the enzymatic activity which converts one μ mole of glucose to gluconic acid and $H_2O_2$ by reaction with glucose at 35° C at pH 5.1 for one minute]

EXAMPLE 32

A water-insoluble tannin preparation [i.e. chinese gallotannin covalently bound to cellulose through the linkage —CONH—$(CH_2)_6$—NHCO—] is prepared in the same manner as described in Example 6-(2). 50 mg of hesperiginase (total activity: 1,900 units) dissolved in 100 ml of a 0.01 M acetate buffer solution (pH 4.3) are added to 500 mg (wet form) of the water-insoluble tannin preparation, and the mixture is stirred at 35° C for 30 minutes. Then, the precipitates are collected by filtration and washed with water. 500 mg (wet form) of an immobilized hesperiginase preparation [i.e. hesperiginase adsorbed on the water-insoluble tannin preparation] are thereby obtained. It shows the hesperiginase activity of 703 units. [One unit of hesperiginase is defined as the enzymatic activity which produces one mg of ramnose by reaction with 0.1% hesperidin at 40° C at pH 3.8 for 30 minutes.]

EXAMPLE 33

A water-insoluble tannin preparation [i.e. chinese gallotannin covalently bound to cellulose through the linkage —$CH_2CH(OH)CH_2NH$—$(CH_2)_6$—$NHCH_2CH(OH)CH_2$—] is prepared in the same manner as described in Example 1-(2). A solution (pH 4.3) of 6 mg of amylase (total activity: 3,600 units) obtained from Bacillus subtilis, in 20 ml of water is added to one g (wet form) of the water-insoluble tannin preparation, and the mixture is stirred at 20° C for 2 hours. Then, the precipitates are collected by filtration and washed with water. 0.98 g (wet form) of an immobilized amylase preparation [i.e. amylase adsorbed on the water-insoluble tannin preparation] are thereby obtained. It shows an amylase activity of 480 units. Amylase activity is estimated by reaction with one % soluble starch at 40° C for 10 minutes, and then coloring said starch with iodine. [One unit of amylase is defined as the enzymatic activity which fades one % of the characteristic blue color of said starch per minute.]

EXAMPLE 34

A water-insoluble tannin preparation [i.e. chinese gallotannin covalently bound to cellulose through the linkage —$CH_2CH(OH)CH_2NH$—$(CH_2)_6$—$NHCH_2CH(OH)CH_2$—] is prepared in the same manner as described in Example 1-(2). 100 mg of $\beta$-galactosidase (total activity: 184 units) dissolved in 4 ml of an aqueous 0.2 M sodium chloride solution are added to one g (wet form) of the water-insoluble tannin preparation, and the mixture is stirred at 25° C for 30 minutes. Then, the precipitates are collected by filtration and washed with water. 0.97 g (wet form) of an immobilized $\beta$-galactosidase preparation [i.e. $\beta$-galactosidase adsorbed on the water-insoluble tannin preparation] are thereby obtained. It shows a $\beta$-galactosidase activity of 75 units. [One unit of $\beta$-galactosidase is defined as the enzymatic activity which produces one $\mu$ mole of o-nitrophenol by reaction with o-nitrophenol-$\beta$-galactopyranoside at 37° C at pH 6.5 for one minute].

EXAMPLE 35

A water-insoluble tannin preparation [i.e. chinese gallotannin covalently bound to cellulose through the linkage —$CH_2$—$CH(OH)CH_2NH$—$(CH_2)_6$—$NHCH_2CH(OH)CH_2$—] is prepared in the same manner as described in Example 1-(2). 4 ml of an aqueous solution of aspartase (total activity: 40,000 $\mu$ moles/hr) are added to one g (wet form) of the water-insoluble tannin preparation, and the mixture is shaken at 25° for 30 minutes. Then, the precipitates are collected by filtration and washed with water. 1.05 g (wet form) of an immobilized aspartase preparation [i.e. aspartase adsorbed on the water-insoluble tannin preparation] are thereby obtained. It shows the aspartase activity of 14,410 $\mu$ moles per hour. [Aspartase activity is indicated in terms of micromoles of L-aspartic acid which are produced by reacting with 1 M ammonium fumarate at 37° C at pH 8.5].

EXAMPLE 36

A water-insoluble tannin preparation [i.e. chinese gallotannin covalently bound to cellulose through the linkage —$CH_2$—$CH(OH)CH_2NH$—$(CH_2)_6$—$NHCH_2CH(OH)CH_2$—] is prepared in the same manner as described in Example 1-(2). 5 ml of an aqueous solution of fumarase (total activity: 43,000 $\mu$ moles/hr) obtained from Brevibacterium ammoniagenes are added to one g (wet form) of the water-insoluble tannin preparation, and the mixture is shaken at 25° C for 30 minutes. Then, the precipitates are collected by filtration and washed with water. 0.98 g (wet form) of an immobilized fumarase preparation [i.e. fumarase adsorbed on the water-insoluble tannin preparation] are thereby obtained. It shows a fumarase activity of 7,300 $\mu$ moles/hr. [Fumarase activity is indicated in terms of micromoles of L-malic acid which are produced by reaction with 0.2 M sodium fumarate at 37° C at pH 7.0].

EXAMPLE 37

A water-insoluble tannin preparation [i.e. chinese gallotannin covalently bound to cellulose through the linkage —$CH_2$—$CH(OH)CH_2NH$—$(CH_2)_6$—$NHCH_2CH(OH)CH_2$—] is prepared in the same manner as described in Example 1-(2). 4 ml of an aqueous solution of L-aspartic acid $\beta$-decarboxylase (total activity: 5,640 $\mu$ moles/hr) obtained from Pseudomonas dacunhae are added to one g (wet form) of the water-insoluble tannin preparation, and the mixture is shaken at 25° C for 30 minutes. Then, the precipitates are collected by filtration and washed with water. 0.95 g (wet form) of an immobilized L-aspartic acid $\beta$-decarboxylase preparation [i.e. L-aspartic acid $\beta$-decarboxylase adsorbed on the water-insoluble tannin preparation] are thereby obtained. It shows a L-aspartic acid $\beta$-decarboxylase activity of 180 $\mu$ moles/hr. [Aspartic acid $\beta$-decarboxylase activity is indicated in terms of micromoles of L-alanine which are produced by reaction with 0.2 M L-aspartic acid at 37° C at pH 5.5].

EXAMPLE 38

A water-insoluble tannin preparation [i.e. chinese gallotannin covalently bound to cellulose through the linkage —$CH_2$—$CH(OH)CH_2NH$—$(CH_2)_6$—$NHCH_2CH(OH)CH_2$—] is prepared in the same manner as described in Example 1-(2). 2 ml of an aqueous solution of aspartase (total activity: 20,000 $\mu$ moles/hr) obtained from Pseudomonas dacunhae are added to one g (wet form) of the water-insoluble tannin preparation, and the mixture is shaken at 25° C for 30 minutes. Then, the precipitates are collected by filtration and washed with water. 1.0 g (wet form) of an immobilized enzyme preparation [i.e. the enzymes adsorbed on the water-insoluble tannin preparation] is thereby obtained. It shows a L-alanine-productivity of 180 $\mu$ moles/hr. [The L-alanine-productivity is indicated in terms of micromoles of L-alanine which are produced by reaction with 0.2 M aspartic acid at 37° C at pH 5.5].

EXAMPLE 39

(1) 4 g of cellulose powder are immersed in 200 ml of an aqueous 25% sodium hydroxide solution at 25° C for 30 minutes, and then washed with water. 10 g of the wet cellulose are suspended in 80 ml of an aqueous 0.1 M sodium bicarbonate solution. The suspension is adjusted to pH 11.5. Cyanogen bromide is added to the suspension (the amount of cyanogen bromide is shown in Table 1), and the mixture is stirred at below 30° C for about 8 minutes. During the reaction, the mixture is kept at a pH of 11 to 11.5 with an aqueous 5 N sodium hydroxide solution. Then, the precipitates are collected by filtration, and washed first with an aqueous 0.1 M sodium bicarbonate solution cooled to about 10° C and then with cool water. The cyanogen bromide-activated cellulose thus obtained is suspended in 100 ml of an aqueous solution (pH 10) containing hexamethylenediamine (hexamethylenediamine content: 2.3 g/100 ml), and the suspension is stirred at 25° C for 2 hours. After the reaction, precipitates are collected by filtration and washed first with an aqueous 0.1 M sodium bicarbonate solution and then with water 10.5 g (wet form) of aminohexylcellulose are obtained.

(2) Cyanogen bromide is added to an aqueous 5% chinese gallotannin solution of pH 11.5. The amount of cyanogen bromide and chinese gallotannin used are shown in Table 1. The mixture is stirred at 20° C for 8 minutes and the mixture is kept at a pH of 11 to 11.5 during the reaction. The cyanogen bromide-activated chinese gallotannin solution thus obtained is added to the aminohexyl-cellulose obtained in paragraph (1), and the mixture is stirred at 25° C for 2 hours. Then, the precipitates are collected by filtration and washed first with an aqueous 0.1 M sodium bicarbonate solution and then with water. 11.2 g (wet form) of a water-insoluble tannin preparation [i.e. chinese gallotannin covalently bound to cellulose through the linkage —CONH—$(CH_2)_6$—NHCO—] are thereby obtained.

(3) 200 mg of aminoacylase (total activity: 4,000 μ moles/hr) are dissolved in 6 ml of an aqueous 0.2 M sodium chloride solution containing 2 v/v % of n-butanol. 500 mg (wet form) of the water-insoluble tannin preparation obtained in paragraph (2) are added to the solution, and the mixture is stirred at 37° C for 30 minutes. Then, the precipitates are collected by filtration and washed with water. 530 mg (wet form) of an immobilized aminoacylase preparation [i.e. aminoacylase adsorbed on the water-insoluble tannin preparation] are obtained. Aminoacylase activity of the immobilized preparation is shown in Table 1

Table 1

| Experiment No. | The amount of cyanogen bromide used in paragraph (1) (g) | The amount of chinese gallotannin and cyanogen bromide used in paragraph (2) | | Aminoacylase activity of the immobilized preparation* |
|---|---|---|---|---|
| | | Chinese gallotannin (g) | Cyanogen bromide (g) | |
| (i) | 0.4 | 1.5 | 0.02 | 8,480 |
| (ii) | 0.4 | 2.6 | 0.04 | 9,056 |
| (iii) | 0.4 | 5.2 | 0.1 | 9,280 |
| (iv) | 0.4 | 21.0 | 0.4 | 10,080 |
| (v) | 0.2 | 10.5 | 0.2 | 10,400 |
| (vi) | 0.1 | 5.2 | 0.1 | 6,176 |
| (vii) | 0.05 | 2.6 | 0.05 | 3,136 |
| (viii) | 0.02 | 1.05 | 0.02 | 2,176 |

Note:
*μmole/hr/10 g (wet form) of the water insoluble tannin preparation

EXAMPLE 40

96 mg of aminoacylase (total activity: 1920 μ moles/hr) are dissolved in 12 ml of an aqueous sodium chloride solution as shown in Table 2. The solution is adjusted to pH 8.0 with NaOH. 250 mg (wet form) of a water insoluble tannin preparation [i.e. chinese gallotannin covalently bound to cellulose through the linkage —CONH—$(CH_2)_6$—NHCO—] prepared in the same manner as described in Experiment (v) of Example 39 are added to the solution, and the mixture is stirred at 25° C for 30 minutes. Then, the precipitates are collected by filtration and washed with water. 260 mg (wet form) of an immobilized aminoacylase preparation [i.e. aminoacylase adsorbed on the water-insoluble tannin preparation] are thereby obtained. Aminoacylase activity of the immobilized preparation is shown in Table 2.

Table 2

| The concentration of sodium chloride (w/v%) | Aminoacylase activity of the immobilized preparation (μ mole per hour per 10 g (wet form) of the water-insoluble tannin preparation) |
|---|---|
| 0 | 1,100 |
| 0.05 | 4,300 |
| 0.1 | 10,550 |
| 0.2 | 11,050 |
| 0.3 | 10,900 |

Table 2-continued

| The concentration of sodium chloride (w/v%) | Aminoacylase activity of the immobilized preparation (μ mole per hour per 10 g (wet form) of the water-insoluble tannin preparation) |
|---|---|
| 0.4 | 10,100 |
| 0.5 | 8,800 |

EXAMPLE 41

96 mg of aminoacylase (total activity: 1,920 μ moles/hr) are dissolved in 12 ml of an aqueous 0.2 M sodium chloride solution. The solution is adjusted to pH 8.0, and ethylene glycol, n-butanol or urea (in the amount shown in Table 3) is added thereto. 200 mg (wet form) of a water-insoluble tannin preparation [i.e. chinese gallotannin covalently bound to cellulose through the linkage —CONH—$(CH_2)_6$—NHCO—] prepared in the same manner as described in Example 6-(2) are added to the solution, and the mixture is shaken at 4° C for 30 minutes. Then, the precipitates are collected by filtration and washed with water. 210 mg (wet form) of an immobilized aminoacylase preparation [i.e. aminoacylase adsorbed on the water-insoluble tannin preparation] are obtained. Aminoacylase activity of the immobilized preparation is shown in Table 3.

Table 3

| Compounds added and concentration (w/v%) thereof | | Aminoacylase activity of the immobilized preparation (μ mole per hour per 200 mg (wet form) of the water-insoluble tannin preparation) |
|---|---|---|
| Ethylene glycol | 50% | 120 |
| | 30% | 140 |
| | 17% | 128 |
| | 8% | 140 |
| n-Butanol | 8% | 172 |
| | 4% | 186 |
| | 2% | 172 |
| | 1% | 172 |
| Urea | 2 M | 140 |
| | 1.3 M | 148 |
| | 0.6 M | 168 |
| | 0.3 M | 140 |
| No addition | | 128 |

EXAMPLE 42

32 mg of aminoacylase (total activity: 640 μ moles/hr) are dissolved in 4 ml of water, and the solution is adjusted to a pH shown in Table 4. 200 mg (wet form) of a water-insoluble tannin preparation [i.e. chinese gallotannin covalently bound to cellulose through the linkage —CONH—$(CH_2)_6$—NHCO—] prepared in the same manner as described in Example 6-(2) are added to the solution, and the mixture is stirred at 25° C for 30 minutes. Then, the precipitates are collected by filtration and washed with water. 200 mg (wet form) of an immobilized aminoacylase preparation [i.e. aminoacylase adsorbed on the water-insoluble tannin preparation] are thereby obtained. Aminoacylase activity of the immobilized preparation is shown in Table 4.

Table 4

| pH | Aminoacylase activity of the immobilized preparation (μ mole per hour per 200 mg (wet form) of the water-insoluble tannin preparation) |
|---|---|
| 4 | 17 |
| 5 | 34 |
| 6 | 45 |

Table 4-continued

| pH | Aminoacylase activity of the immobilized preparation (μ mole per hour per 200 mg (wet form) of the water-insoluble tannin preparation) |
|----|---|
| 7 | 58 |
| 8 | 62 |
| 9 | 64 |
| 10 | 58 |
| 11 | 28 |

EXAMPLE 43

96 mg of aminoacylase (total activity: 1,920 μ moles/hr) are dissolved in 12 ml of an aqueous 0.2 M sodium chloride solution. 0.2 ml of n-butanol are added to the solution, and the solution is adjusted to pH 8.0. 200 mg (wet form) of a water-insoluble tannin preparation [i.e. chinese gallotannin covalently bound to cellulose through the linkage —CONH—$(CH_2)_6$—NHCO—] prepared in the same manner as described in Example 6-(2) are added to the solution, and the mixture is stirred for 30 minutes at a temperature shown in Table 5. Then, the precipitates are collected by filtration and washed with water. 210 mg (wet form) of an immobilized aminoacylase [i.e. aminoacylase adsorbed on the water-insoluble tannin preparation] are thereby obtained. Aminoacylase activity of the immobilized preparation is shown in Table 5.

Table 5

| Temperature | Aminoacylase activity of the immobilized preparation (μ mole per hour per 200 mg (wet form) of the water-insoluble tannin preparation) |
|---|---|
| 4° C | 184 |
| 25° C | 280 |
| 37° C | 280 |
| 45° C | 291 |

EXAMPLE 44

(1) 2 g of aminoacylase (total activity: 40,000 μ moles/hr) are dissolved in 250 ml of an aqueous 0.2 M sodium chloride solution containing 2 v/v % of n-butanol. The solution is adjusted to pH 8.0. 5 g (wet form) of a water-insoluble tannin preparation [i.e. chinese gallotannin covalently bound to cellulose through the linkage —CONH—$(CH_2)_6$—NHCO—] prepared in the same manner as described in Example 6-(2) are added to the solution, and the mixture is stirred at 25° C for 1 hours. Then, the precipitates are collected by filtration and washed with water. 5.2 g (wet form) of an immobilized aminoacylase preparation [i.e. aminoacylase adsorbed on the water-insoluble tannin preparation] are thereby obtained.

(2) A column of 0.5 cm in diameter and 10 cm in height is charged with 2 g (wet form) of the immobilized aminoacylase preparation obtained in paragraph (1). Then, an aqueous 0.6 M N-acetyl-DL-methionine solution (pH 7.0, 5 × $10^{-4}$ M $Co^{++}$) or an aqueous 0.2 M N-acetyl-DL-tryptophan solution (pH 7.0, 5 × $10^{-4}$ M $Co^{++}$) is passed through the column at a flow rate of 1.7 ml/hr and 2.0 ml/hr, respectively. The amount of L-methionine or L-tryptophan in the effluent is measured at intervals, and the aminoacylase activity of the immobilized preparation is calculated therefrom. The results are shown in Table 6.

Table 6

| Operation time (days) | 0.6 M N-acetyl-DL-methionine Aminoacylase activity (μ mole/hr) | 0.2 M N-acetyl-DL-tryptophan Aminoacylase activity (μ mole/hr) |
|---|---|---|
| 0 | 1,512 (100) | 972 (100) |
| 2 | 1,836 (121) | 1,138 (117) |
| 6 | 1,174 (78) | 731 (75) |
| 10 | 1,315 (87) | 731 (75) |
| 17 | 962 (64) | 498 (51) |
| 18 | 1,047 (69) | 435 (45) |
| 22 | 1,106 (73) | 554 (57) |
| 26 | 1,106 (73) | 499 (51) |
| 30 | 976 (65) | 523 (54) |
| 34 | 749 (50) | 515 (53) |
| 40 | 599 (40) | 515 (53) |
| 44 | 623 (41) | 488 (50) |

Note: Numerical values shown in parentheses stand for the potency ratio of the enzymatic activity calculated by the following formula:

$$\left[\frac{\text{Activity of the immobilized aminoacylase preparation estimated after a period of time specified in Table 6}}{\text{Initial activity of the immobilized aminoacylase preparation}}\right] \times 100$$

EXAMPLE 45

A column of 0.3 cm in diameter and 5 cm in height is charged with one ml of the water-insoluble tannin preparation obtained in Example 17. The column is washed first with 100 ml of a 0.1 M carbonate buffer solution, then with 50 ml of water and finally with 50 ml of an acetate buffer solution (pH 4.3, 1 m mho). An enzyme shown in Table 7 is dissolved in an acetate buffer solution (pH 4.3, 1 m mho), and 200 ml of said enzyme solution having a protein content of one mg/ml (hereinafter referred to as "sample solution") are passed through the column at a flow rate of 20 ml/hr. The column is washed with a 0.1 M acetate buffer solution (pH 4.3) and water. Then, the column is eluted with a carbonate buffer solution (pH 10, 50 mho), and the amount of protein in the eluate (i.e., the amount of protein adsorbed on the water-insoluble tannin preparation) is measured by the Copper-Folin method. Further, just for comparison, the amount of protein adsorbed on aminohexyl-cellulose (manufactured by Merck Co. under the trade name "AH-Cellulose") is measured by treating said cellulose in the same manner as above. The results are shown in Table 7.

Table 7

| Enzyme | Amount of protein adsorbed on the water-insoluble tannin preparation (mg/ml) | Recovery yield * (%) | Amount of protein adsorbed on "AH-Cellulose" (mg/ml) |
|---|---|---|---|
| lysozyme | 37.0 | 89 | 0.2 |
| trypsin | 96.0 | 94 | 0.2 |
| asparaginase | 47.4 | 95 | 0.1 |
| α-amylase | 51.6 | 75 | 0.5 |
| acidic phosphatase | 37.4 | 94 | 1.1 |

Note: * "Recovery yield (%)" shown in Table 7 is calculated by the following formula:

$$\left[\frac{\text{Total activity of the enzyme contained in the eluate}}{\text{(Total activity of the sample solution) } - \text{ (Total activity of the enzyme not adsorbed on the water-insoluble tannin preparation)}}\right] \times 100$$

EXAMPLE 46

A column of 0.3 cm in diameter and 5 cm in height is charged with one ml of the water-insoluble tannin preparation obtained in Example 13-(2). The column is washed first with 50 ml of an aqueous 1 M sodium chloride solution and then with 30 ml of a phosphate buffer solution (pH 7.0, 1 m mho). A test material shown in Table 8 is dissolved in a phosphate buffer solution (pH 7.0, 1 m mho). 2 ml of the test material solution (test material content: 1 μ mole/ml) are passed through the column, and the column is washed with 15 ml of a phosphate buffer solution (pH 7.0, 1 m mho). Then, the amount of the test material contained in the effluent and washing solution is measured, and the amount of said material adsorbed on the water-insoluble tannin preparation is calculated therefrom. The results are shown in Table 8.

Table 8

| Test materials | Amount of a test material adsorbed on the water-insoluble tannin preparation (μ g/ml) |
|---|---|
| (Proteins) | |
| α-amylase | 12,000 |
| egg-albumin | 7,000 |
| α-globulin | 30,000 |
| (L-Amino Acids) | |
| arginine | 1.0 |
| histidine | 0 |
| alanine | 2.1 |
| leucine | 5.8 |
| isoleucine | 0 |
| valine | 9.6 |
| tryptophan | 2.2 |
| asparagine | 3.6 |
| aspartic acid | 6.9 |
| (Organic Acids) | |
| fumaric acid | 0 |
| L-malic acid | 0 |
| (Saccharides) | |
| glucose | 0 |
| fructose | 0 |
| ribose | 0 |
| (Nucleosides) | |
| adenosine | 0 |
| guanidine | 0 |
| cytidine | 0 |
| uridine | 0 |
| thymidine | 0 |

EXAMPLE 47

A column of 0.3 cm in diameter and 5 cm in height is charged with one ml of the water-insoluble tannin preparation obtained in Example 17. The column is washed first with 5 ml of an aqueous 0.1 M sodium chloride solution and then with a phosphate buffer solution (pH 7.0, 1 m mho). A test material shown in Table 9 is dissolved in a phosphate buffer solution (pH 7.0, 1 m mho). 2 ml of said test material solution (test material content: 1 μ mole/ml) are passed through the column, and the column is washed with 15 ml of a phosphate buffer solution (pH 7.0, 1 m mho). Then, the amount of the test material contained in the effluent and washing solution is measured, and the amount of said material adsorbed on the water-insoluble tannin preparation is calculated therefrom. The results are shown in Table 9.

Table 9

| Test materials | Amount of a test material adsorbed on the water-insoluble tannin preparation (μ g/ml) |
|---|---|
| (Proteins) | |
| asparaginase | 41,000 |
| acidic phosphatase | 39,000 |
| lysozyme | 11,000 |
| (L-Amino acids) | |
| arginine | 1.5 |
| histidine | 1.9 |
| alanine | 2.3 |
| valine | 4.9 |
| aspartic acid | 3.7 |
| tryptophan | 2.3 |
| (Organic acids) | |
| fumaric acid | 0 |
| L-malic acid | 0 |
| (Saccharides) | |
| glucose | 0 |
| fructose | 0 |
| (Nucleosides) | |
| adenosine | 0 |
| guanosine | 0 |
| cytidine | 0 |
| uridine | 0 |
| thymidine | 0 |

EXAMPLE 48

A column of 0.3 cm in diameter and 5 cm in height is charged with one ml of the water-insoluble tannin preparation obtained in Example 16-(2). The column is washed first with 50 ml of a 0.1 M carbonate buffer solution (pH 10, 50 m mho), then with 100 ml of water and finally with 50 ml of a carbonate buffer solution (pH 9.0, 1 m mho). A sample solution (protein content: 100 μ g/ml) is made by dissolving lysozyme in a carbonate buffer solution (pH 9.0, 1 m mho), and 980 ml of said sample solution are passed through the column. At the end point of the operation, the concentration of protein in the effluent becomes equal to that of the protein contained in the sample solution. Then, the column is eluted with an aqueous 0.01 N-sodium hydroxide solution cooled to about 4° C. The eluate thus obtained contains 23.2 mg of protein. Recovery yield: 96%

EXAMPLE 49

Lysozyme is treated in the same manner as described in Example 48 except that one ml of the water-insoluble tannin preparation obtained in Example 17 is employed instead of the water-insoluble preparation of Example 16. The eluate thus obtained contains 54 mg of protein. Recovery yeild: 97%

EXAMPLE 50

A column of 0.3 cm in diameter and 5 cm in height is charged with one ml of the water-insoluble tannin preparation obtained in Example 17. The column is washed first with 100 ml of a 0.1 M carbonate buffer solution, then with 50 ml of water and finally with an acetate buffer solution (pH 4.3, 1 m mho). A sample solution (protein content: 100 μ g/ml) is made by dissolving in an acetate buffer solution (pH 4.3, 1 m mho), and 1,200 ml of said sample solution are passed through the column. At the final stage of the operation, the concentration of protein in the effluent becomes equal to that of the protein contained in the sample solution. Then, the column is eluted with an aqueous 0.01 N-sodium hydroxide solution cooled at about 4° C. The eluate thus obtained contains 48.7 mg of protein. Recovery yield: 75%

EXAMPLE 51

A column of 0.3 cm in diameter and 5 cm in height is charged with one ml of the water-insoluble tannin preparation obtained in Example 18-(1). The column is washed first with a 0.1 M carbonate buffer solution (pH 10, 50 m mho), then with 100 ml of water and finally with 50 ml of an acetate buffer solution (pH 5.5, 1 m mho). A sample solution (protein content: 100 μ g/ml) is made by dissolving trypsin in an acetate buffer solution (pH 5.5, 1 m mho), and 540 ml of the sample solution is passed through the column at a flow rate of 30 ml/hr. At the final state of the operation, the concentration of protein in the effluent becomes equal to that of the protein contained in the sample solution. Then, the column is eluted with an aqueous 1 M sodium chloride solution. The eluate thus obtained contains 8.9 mg of protein. Recovery yield: 98%

EXAMPLE 52

A column of 0.3 cm in diameter and 5 cm in height is charged with one ml of the water-insoluble tannin preparation obtained in Example 17. The column is washed first with 50 ml of a 0.1 M carbonate buffer solution (pH 10, 50 m mho), then with 100 ml of water and finally with 50 ml of a carbonate buffer solution (pH 9.0, 1 m mho). A sample solution is made by dissolving 10 mg of lysozyme, 10 mg of L-arginine, 10 mg of L-histidine, 10 mg of L-alanine, 10 mg of L-leucine, 10 mg of L-valine, 10 mg of L-tryptophan and 10 mg of L-aspartic acid in 200 ml of a carbonate buffer solution (pH 9.0, 1 m mho), and the sample solution is passed through the column. The effluent thus obtained shows no turbidity when heated at 60° C for 10 minutes and then allowed to stand at room temperature for one week. On the other hand, the sample solution not passed through the column becomes turbid upon heating at 60° C for 10 minutes and, when allowed to stand at room temperature for one week, it gives an insoluble white precipitate. Further, the results of an amino acid analysis show that the effluent contains the same amount of amino acids as does the above-mentioned sample solution. From these facts it is clear that the lysozyme is adsorbed on the water-insoluble tannin preparation, but the amino acids are not.

EXAMPLE 53

A column of 0.3 cm in diameter and 5 cm in height is charged with one ml of the water-insoluble tannin preparation obtained in Example 17. The column is washed first with 50 ml of a 0.1 M carbonate buffer solution (pH 10, 50 m mho), then with 100 ml of water and finally with 50 ml of a carbonate buffer solution (pH 9.0, 1 m mho). A sample solution is made by dissolving 20 mg of lysozyme, 20 mg of fumaric acid and 20 mg of L-malic acid in 200 ml of a carbonate buffer solution (pH 9.0, 1 m mho), and the sample solution is passed through the column. The effluent thus obtained does not contain any substantial amount of protein. Further, the effluent contains the same amount of organic acids as does the above-mentioned sample solution.

EXAMPLE 54

A column of 0.3 cm in diameter and 5 cm in height is charged with one ml of the water-insoluble tannin preparation obtained in Example 17. The column is washed first with 100 ml of a 0.1 M carbonate buffer solution (pH 10), then with 50 ml of water and finally with 50 ml of an acetate buffer solution (pH 5.5, 1 m mho). A sample solution is made by dissolving 10 mg of α-amylase, 0.1 mg of L-arginine, 0.1 mg of L-histidine, 0.1 mg of L-alanine, 0.1 mg of L-leucine, 0.1 mg of L-valine, 0.1 mg of L-tryptophan, 0.1 mg of L-asparagine and 0.1 mg of L-aspartic acid in 200 ml of an acetate buffer solution (pH 5.5, 1 m mho), and the sample solution is passed through the column. The effluent thus obtained shows no turbidity when heated at 60° C for 10 minutes. On the other hand, the sample solution not passed through the column becomes turbid when heated under the same conditions stated above. Further, the results of the amino acid analysis shows that the effluent contains the same amount of amino acids as does the above-mentioned sample solution.

EXAMPLE 55

One ml of the water-insoluble tannin preparation obtained in Example 17 is added to 500 ml of a Tris buffer solution (pH 7.0, 1 m mho) containing 100 μ g/ml of crystalline asparaginase (obtained from Proteus vulgaris). The mixture is stirred for 4 hours under cooling and then filtered to separate the water-insoluble tannin preparation. The filtrate contains 4.5 μ g/ml of protein. Then, the water-insoluble tannin preparation is eluted with a 1 M sodium chloride solution. The eluate thus obtained contains 45.5 mg of protein.

EXAMPLE 56

An aqueous asparaginase solution (hereinafter referred to as "sample solution") is prepared from Proteus vulgaris according to the method described in Biochemistry 11, 217–222 (1972). The sample solution (pH 8.0, 4 m mho, protein content: 23.2 mg/ml, asparaginase activity: 13.9 units/ml) is adjusted to pH 7.0 with an aqueous sodium hydroxide solution and then diluted with a 5-fold volume of water. A column (1 cm in diameter and 10 cm in height) is charged with 5 ml of the water-insoluble tannin preparation obtained in Example 16-(1), and 300 ml of the diluted solution are passed through the column. 152 units of asparaginase are thereby adsorbed on the water-insoluble tannin preparation. After the column is washed with 50 ml of a Tris buffer solution (pH 7.0, 1 m mho), it is eluted with 50 ml of a phosphate buffer solution (pH 7.0, 5 m mho) containing 0.05 M L-asparagine. 24 ml of the eluate thus obtained contains 42 mg of protein, and said eluate shows the asparaginase activity of 149 units. This indicates that 98% of asparaginase adsorbed on the water-insoluble tannin preparation are eluted with the phosphate buffer solution and the protein in the eluate shows an asparaginase activity about 6 times higher than that of the protein contained in the abovementioned sample solution. [One unit is defined as the enzymatic activity which affords one micromole of ammonia by reaction with 0.03 M L-asparagine at 37° C at pH 8.0 for one minute]

EXAMPLE 57

A hesperiginase solution (hereinafter referred to as the "sample solution") is prepared by filtering a fermentation broth of Aspergillus niger. The sample solution (pH 4.8, 14 m mho, protein content: 19.2 mg/ml, hesperiginase activity: 8.6 units/ml) is adjusted to pH 7.0 with an aqueous sodium hydroxide solution and then diluted with a 5-fold volume of water. A column (1 cm in diameter and 10 cm in height) is charged with 5 ml of the water-insoluble tannin preparation obtained in Example 17, and 400 ml of the diluted solution (total activity: 1,242 units) are passed through the column. 270 units of hesperiginase are thereby adsorbed on the water-insoluble tannin preparation. After the column is washed with 50 ml of a Tris buffer solution (pH 7.0, 1 m mho), said column is eluted with 50 ml of a carbonate buffer solution (pH 10, 50 m mho). 25 ml of the eluate thus obtainted contains 42 mg of protein, and said eluate shows the hesperiginase activity of 149 units. This indicates that 98% of hesperiginase adsorbed on the water-insoluble tannin preparation is eluted with the carbonate buffer solution and the protein in the eluate shows a hesperiginase activity about 2 times higher than that of the protein contained in the above-mentioned sample solution.

EXAMPLE 58

A column (1 cm in diameter and 10 cm in height) is charged with 5 ml of the water-insoluble tannin preparation obtained in Example 16-(1). The column is washed first with one liter of a 0.1 M carbonate buffer solution (pH 10) and then with one liter of water. Amylase (manufactured by Tanabe Seiyaku Co., Ltd. under the trade designation "Morotomine") is dissolved in Japanese sake (a fermented liquor made from rice), the solution (pH 4.3, 0.6 m mho, protein content: 100 μ g/ml), hereinafter referred to as the "sample solution," is passed through the column under cooling, and 500 ml of the effluent are collected. The effluent thus obtained shows no turbidity when heated at 60° C for 10 minutes and then allowed to stand at room temperature for 50 days. On the other hand, the sample solution not passed through the column becomes turbid when treated under the same conditions stated above. Further, the effluent contains the same amount of each of amino acids, saccharides and organic acids as in case of the abovementioned Japanese sake.

After the above-mentioned operations, the column is eluted with 0.01 N-hydrochloric acid. 104 mg of amylase are thereby recovered.

EXAMPLE 59

(1) 10.5 g (wet form) of aminohexyl-cellulose are prepared from 4 g of cellulose powder in the same manner as described in Example 1-(1). 100 ml of an aqueous 5% chinese gallotannin solution (pH 5, 7 or 9) are added to 4 g (dry form) of the aminohexyl-cellulose, and the mixture is stirred at 25° C for 2 hours. Then, the precipitates are collected by filtration and washed with water. 12.5 g (wet form) of a water-insoluble tannin preparation [i.e. chinese gallotannin adsorbed on the aminohexyl-cellulose] are thereby obtained.

(2) 500 mg (wet form) of the water-insoluble tannin preparation obtained in paragraph (1) and 200 mg of aminoacylase (total activity: 4,000 μ moles/hr) or 25 mg of glucose isomerase (total activity: 690 units) are treated in the same manner as described in Example 1-(3) or Example 28. An immobilized aminoacylase or glucose isomerase preparation is obtained. Enzymatic activity of said immobilized preparation is shown in Table 10.

Table 10

| pH of the chinese gallotannin solution | Enzymatic activity of the immobilized preparation | |
|---|---|---|
| | Aminoacylase activity* | Glucose isomerase activity** |
| 5 | 7,650 | 9 |
| 7 | 9,054 | 45 |
| 9 | 9,468 | 237 |

Note:
*μmole per hour per 10 g (wet form) of the water-insoluble tannin preparation
**mg per hour per 100 mg (wet form) of the water-insoluble tannin preparation

EXAMPLE 60

(1) 11.0 (wet form) of n-octyl-cellulose [i.e. cellulose-O—$CH_2CH(OH)CH_2NH$—$(CH_2)_7$—$CH_3$] are prepared by treating 4 g of cellulose powder (trade designation "Cellulose Powder C") in the same manner as described in Example 1-(1) except that 1.2 ml of n-octylamine are used instead of hexamethylenediamine. 4 g (dry form) of the n-octyl-cellulose are added to 100 ml of an aqueous 5% chinese gallotannin solution (pH 7.0), and the mixture is stirred at 25° C for 2 hours. Then, the precipitates are collected by filtration and washed with water. 12.7 g (wet form) of a water-insoluble tannin preparation [i.e. chinese gallotannin adsorbed on the n-octyl-cellulose] is thereby obtained.

(2) 500 mg (wet form) of the water-insoluble tannin preparation obtained in paragraph (1) and 200 mg of aminoacylase are treated in the same manner as described in Example 1-(3). An immobilized aminoacylase preparation is obtained. It shows an aminoacylase activity of 14,400 μ moles per hour per 10 g (wet form) of the water-insoluble tannin preparation.

EXAMPLE 61

(1) 10.9 (wet form) of n-dodecyl-cellulose [i.e. cellulose-O—$CH_2CH(OH)CH_2NH$—$(CH_2)_{11}$—$CH_3$] are prepared by treating 4 g of cellulose powder (trade designation "Cellulose Powder C") in the same manner as described in Example 1-(1) except that 1.5 g of n-dodecylamine are used instead of hexamethylenediamine. 4 g (dry form) of the n-dodecyl-cellulose are added to 100 ml of an aqueous 5% chinese gallotannin solution (pH 7.0), and the mixture is stirred at 25° C for 2 hours. Then, the precipitates are collected by filtration and washed with water. 12.4 g (wet form) of a water-insoluble tannin preparation [i.e. chinese gallotannin adsorbed on the n-dodecylcellulose] are thereby obtained.

(2) 500 mg (wet form) of the water-insoluble tannin preparation obtained in paragraph (1) and 200 mg of aminoacylase are trested in the same manner as described in Example 1-(3). An immobilized aminoacylase preparation is obtained. It shows an aminoacylase activity of 7,389 μ moles per hour per 10 g (wet form) of the water-insoluble tannin preparation.

EXAMPLE 62

(1) 4 g of cellulose powder (manufactured by Toyo Roshi Co. under the trade designation "Cellulose Powder D") are immersed in 15 ml of an aqueous 25% sodium hydroxide solution at 10° C for 30 minutes. Then, 0.5 ml of n-butylglycidyl ether [i.e. n-butyl ether of 2,3-epoxypropanol] and 35 ml of water are added to the wet cellulose, and the mixture is stirred at 60° C for 2 hours. After the reaction, precipitates are collected by filtration and washed with water. 11.1 g of n-butyl-cellulose [i.e. cellulose-O—$CH_2CH(OH)CH_2O$—$(CH_2)_3$—$CH_3$] are thereby obtained. 500 mg (wet form) of the butyl-cellulose are added to 100 ml of an aqueous 5% chinese gallotannin solution (pH 7.0). Then, the precipitates are collected by filtration and washed with water. 12.3 g (wet form) of a water-insoluble tannin preparation [i.e. chinese gallotannin adsorbed on the butyl-cellulose] are thereby obtained.

(2) 500 mg (wet form) of the water-insoluble tannin preparation obtained in paragraph (1) and 200 mg of aminoacylase are treated in the same manner as described in Example 1-(3). An immobilized aminoacylase preparation is obtained. It shows the aminoacylase activity of 11,160 μ moles per hour per 10 g (wet form) of the water-insoluble tannin preparation.

EXAMPLE 63

(1) 4 g of cellulose powder (trade designation "Cellulose Powder D") are immersed in 15 ml of an aqueous 25% sodium hydroxide solution at 10° C for 30 minutes. 0.5 ml of phenyl glycidyl ether (i.e. phenyl ether of 2,3-epoxypropanol) and 35 ml of an aqueous 50% ethanol solution are added to the wet cellulose, and the mixture is stirred at 60° C for 2 hours. After the reaction, phenoxypropyl-cellulose [i.e. cellulose

thus obtained is added to 100 ml of an aqueous 5% chinese gallotannin solution (pH 7.0). Then, the precipitates are collected by filtration and washed with water. 12.1 g (wet form) of a water-insoluble tannin preparation [i.e. chinese gallotannin adsorbed on the phenoxypropyl-cellulose] are thereby obtained.

(2) 500 mg (wet form) of the water-insoluble tannin preparation obtained in paragraph (1) and 200 mg of aminoacylase are treated in the same manner as described in Example 1-(3). An immobilized aminoacylase preparation is obtained. It shows an aminoacylase activity of 12,420 μ moles per hour per 10 g (wet form) of the water-insoluble tannin preparation.

EXAMPLE 64

(1) 14 g (wet form) of aminohexyl-cellulose are prepared from 4 g of cellulose powder (trade designation "Cellulose Powder D") in the same manner as described in Example 1-(1). 100 ml of an aqueous 5% chinese gallotannin solution (pH 7.0) are added to 4 g (dry form) of the aminohexyl-cellulose, and the mixture is stirred at 25° C for 2 hours. Then, the precipitates are collected by filtration and washed with water. 16.4 g (wet form) of a water-insoluble tannin preparation [i.e. chinese gallotannin adsorbed on the aminohexyl-cellulose] are thereby obtained.

(2) 5 g (wet form) of the water-insoluble tannin preparation obtained in paragraph (1) and 2 g of aminoacylase are treated in the same manner as described in Example 1-(3). 5.5 g (wet form) of an immobilized aminoacylase preparation are obtained.

(3) A column (1 cm in diameter and 10 cm in height) is charged with 2 g (wet form) of the immobilized aminoacylase preparation obtained in paragraph (2). An aqueous 0.6 M N-acetyl-DL-methionine solution (pH 7.0, 5 × 10$^{-4}$ M Co$^{++}$) or an aqueous 0.2 M N-acetyl-DL-tryptophan solution (pH 7.0, 5 × 10$^{-4}$ M Co$^{++}$) is passed through the column at a flow rate of 6 ml/hr. The amount of L-methionine or L-tryptophan in the effluent is measured at intervals, and the aminoacylase activity of the immobilized aminoacylase preparation is calculated therefrom. The results are shown in Table 11.

Table 11

| Operation time (days) | Potency ratio of enzymatic activity* | |
|---|---|---|
| | 0.6 M N-acetyl-DL-methionine | 0.2 M N-acetyl-DL-tryptophan |
| 0 | 100 | 100 |

Table 11-continued

| Operation time (days) | Potency ratio of enzymatic activity* | |
|---|---|---|
| | 0.6 M N-acetyl-DL-methionine | 0.2 M N-acetyl-DL-tryptophan |
| 1 | 145 | 89 |
| 3 | 126 | 76 |
| 7 | 109 | 60 |
| 10 | 82 | 58 |
| 15 | 79 | 50 |

Note:
*The potency ratio of enzymatic activity is calculated by the formula shown in the foot note of Table 6.

EXAMPLE 65

(1) 14.5 g (wet form) of n-octyl-cellulose [i.e. cellulose —O—CH$_2$CH(OH)CH$_2$NH—(CH$_2$)$_7$—CH$_3$] are prepared by treating 4 g of cellulose powder (trade designation "Cellulose Powder D") in the same manner as described in Example 1-(1) except that 1.2 ml of n-octylamine are used instead of hexamethylenediamine. 100 ml of an aqueous 5% chinese gallotannin solution (pH 7.0) are added to 4 g (dry form) of the n-octyl-cellulose, and the mixture is stirred at 25° C for 2 hours. Then, the precipitates are collected by filtration and washed with water. 16.7 g (wet form) of a water-insoluble tannin preparation [i.e. chinese gallotannin adsorbed on the n-octyl-cellulose] are thereby obtained.

(2) 5 g (wet form) of the water-insoluble tannin preparation obtained in paragraph (1) and 2 g of aminoacylase are treated in the same manner as described in Example 1-(3). 5.6 g (wet form) of an immobilized aminoacylase preparation are obtained.

(3) A column (1 cm in diameter and 10 cm in height) is charged with 2 g (wet form) of the immobilized aminoacylase preparation obtained in paragraph (2). An aqueous 0.6 M N-acetyl-DL-methionine solution (pH 7.0, 5 × 10$^{-4}$ M Co$^{++}$) or an aqueous 0.2 M N-acetyl-DL-tryptophan solution (pH 7.0, 5 × 10$^{-4}$ M Co$^{++}$) is passed through the column at a flow rate of 6 ml/hr. The amount of L-methionine or L-tryptophan in the effluent is measured at intervals, and the aminoacylase activity of the immobilized aminoacylase preparation is calculated therefrom. The results are shown in Table 12.

Table 12

| Operation time (days) | Potency ratio of enzymatic activity* | |
|---|---|---|
| | 0.6 M N-acetyl-DL-methionine | 0.2 M N-acetyl-DL-tryptophan |
| 0 | 100 | 100 |
| 1 | 137 | 112 |
| 3 | 121 | 104 |
| 7 | 94 | 87 |
| 10 | 79 | 69 |
| 15 | 79 | 70 |

Note:
*The potency ratio of enzymatic activity is calculated by the formula shown in the foot note of Table 6.

What we claim is:

1. A water-insoluble tannin preparation consisting essentially of tannin covalently bound to a water-insoluble, hydrophilic carrier selected from the group consisting of a hydroxy-polymer, an amino-polymer and a carboxyl-polymer through a diazo linkage or by means of at least one of cyanogen halide, epihalohydrin, α,ω-bis(2,3-epoxypropyl)alkane and α,ω-bis(2,3-epoxypropoxy)alkane.

2. The tannin preparation of claim 1 wherein said cyanogen halide, epihalohydrin, α,ω-bis(2,3-epoxypropyl)alkane and α,ω-bis(2,3-epoxypropoxy)alkane are employed in combination with at least one of alkylenediamine, aminoalkanol, aminoalkanoic acid, alkylenediol and haloalkanoyl halide.

3. A water-insoluble tannin preparation consisting essentially of tannin covalently bound to a water-insoluble, hydrophilic carrier selected from the group consisting of a hydroxy-polymer, an amino-polymer and a carboxyl-polymer through a linkage selected from the group consisting of —CONH—, —CH$_2$CH(OH)CH$_2$—, —CH$_2$CH(OH)CH$_2$—A—CH$_2$CH(OH)CH$_2$—, —Y'λ—(CH$_2$)$_n$—NHCO—, —Y'—(CH$_2$)$_n$—CONH—, —Y'λ—(CH$_2$)$_n$—NHCH$_2$CH(OH)CH$_2$—, —Y'λ—(CH$_2$)$_n$NH(CH$_2$)$_m$CO— and —CONH(CH$_2$)$_n$OCH$_2$CH(OH)CH$_2$—, wherein Y' is —CONH— or —CH$_2$CH(OH)CH$_2$NH—, A is —(CH$_2$)$_q$— or —O(CH$_2$)$_q$O—, each one of n and m is an integer of 1 to 16 and q is an integer of 1 to 6.

4. A water-insoluble tannin preparation consisting essentially of tannin covalently bound to a polysaccharide through a linkage selected from the group consisting of —CH$_2$CH(OH)CH$_2$—, —CH$_2$CH(OH)CH$_2$—A—CH$_2$CH(OH)CH$_2$—, —CH$_2$CH(OH)CH$_2$—NH(CH$_2$)$_n$—Y—, —CONH(CH$_2$)$_n$—Y—, —Y'λ—(CH$_2$)$_n$CONH(CH$_2$)$_m$—Y—, —Y'—(CH$_2$)$_n$NHCO(CH$_2$)$_m$—Y—,

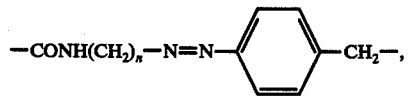

and

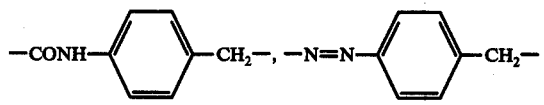

wherein Y is —NHCO—, —NHCH$_2$CH(OH)CH$_2$—, —OCH$_2$CH(OH)CH$_2$— or —NHCOCH$_2$—, Y' is —CONH— or —CH$_2$CH(OH)CH$_2$NH—, each one of n and m is an integer of 1 to 16, A is —(CH$_2$)$_q$— or —O(CH$_2$)$_q$O—, and q is an integer of 1 to 6.

5. The tannin preparation of claim 4 wherein said linkage is —CH$_2$CH(OH)CH$_2$—.

6. The tannin preparation of claim 4 wherein said linkage is —CH$_2$CH(OH)CH$_2$—A—CH$_2$CH(OH)CH$_2$—.

7. The tannin preparation of claim 4 wherein said linkage is —CH$_2$CH(OH)CH$_2$NH(CH$_2$)$_n$—Y—.

8. The tannin preparation of claim 4 wherein said linkage is —CONH(CH$_2$)$_n$—Y—.

9. The tannin preparation of claim 4 wherein said linkage is —Y'—(CH$_2$)$_n$CONH(CH$_2$)$_m$—Y—.

10. The tannin preparation of claim 4 wherein said linkage is —Y'—(CH$_2$)$_n$NHCO(CH$_2$)$_m$—Y—.

11. The tannin preparation of claim 4 wherein said linkage is

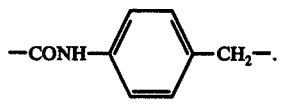

12. The tannin preparation of claim 4 wherein said linkage is

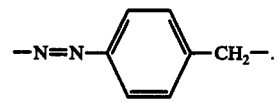

13. The tannin preparation of claim 4 wherein said linkage is

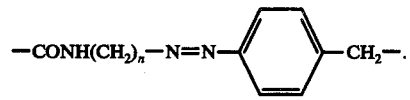

14. A water-insoluble tannin preparation consisting essentially of tannin bound by physical adsorption to an alkyl-polysaccharide represented by the formula:

Polysaccharide-O-CH$_2$CH(OH)CH$_2$O(CH$_2$)$_m$H wherein m is an integer of 1 to 16.

15. A water-insoluble tannin preparation consisting essentially of tannin bound by physical adsorption to an alkyl-polysaccharide represented by the formula:

Polysaccharide—O—CH$_2$CH(OH)CH$_2$NH(CH$_2$)$_m$H wherein m is an integer of 1 to 16.

16. A water-insoluble tannin preparation consisting essentially of tannin bound by physical adsorption to an alkyl-polysaccharide represented by the formula:

Polysaccharide—O—CONH(CH$_2$)$_m$H wherein m is an integer of 1 to 16.

17. A water-insoluble tannin preparation consisting essentially of tannin bound by physical adsorption to a phenoxyalkyl-polysaccharide represented by the formula:

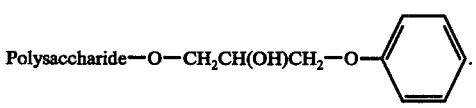

18. A water-insoluble tannin preparation consisting essentially of tannin bound by physical adsorption to an aminoalkyl-polysaccharide represented by the formula:

Polysaccharide—O—CH$_2$CH(OH)CH$_2$NH(CH$_2$)$_m$NH$_2$ wherein m is an integer of 1 to 16.

19. A water-insoluble tannin preparation consisting essentially of tannin bound by physical adsorption to an aminoalkyl-polysaccharide represented by the formula:

Polysaccharide—O—CH$_2$CONH(CH$_2$)$_m$NH$_2$

20. A method of preparing a water-insoluble tannin preparation consisting essentially of tannin bound by covalent linkage to a water-insoluble, hydrophilic carrier selected from the group consisting of a hydroxy-polymer and an amino-polymer, which comprises reacting tannin or said hydroxy- or amino-polymer with cyanogen halide, epihalohydrin, α,ω-bis(2,3-epoxypropyl)alkane or α,ω-bis(2,3-epoxypropoxy)alkane to give an activated tannin or polymer and reacting said activated tannin with said hydroxy- or amino-polymer; or reacting said activated polymer with tannin.

21. A method of preparing a water-insoluble tannin preparation consisting essentially of tannin bound by covalent linkage to a water-insoluble, hydrophilic amino-polymer, which comprises diazotizing said amino-polymer to give a diazotized amino-polymer, and reacting the diazotized amino-polymer with tannin.

22. A method of preparing a water-insoluble tannin preparation consisting essentially of tannin bound by covalent linkage to a water-insoluble, hydrophilic carrier selected from the group consisting of a hydroxy-polymer and an amino-polymer, which comprises:

(A) reacting tannin with cyanogen halide, epihalohydrin, α,ω-bis(2,3-epoxypropyl)alkane or α,ω-bis(2,3-epoxypropoxy)alkane to give an activated tannin, reacting said activated tannin with alkylenediamine or aminoalkanol to give an aminoalkyl- or hydroxyalkyl-tannin, and (B) reacting any of said aminoalkyl-tannin, hydroxyalkyl-tannin, the hydroxy-polymer or the amino-polymer with cyanogen halide, epihalohydrin, α,ω-bis(2,3-epoxypropyl)alkane, α,ω-bis(2,3-epoxypropoxy)alkane or haloalkanoyl halide to give an activated tannin derivative or polymer, and reacting said activated tannin derivative with said hydroxy- or amino-polymer; or reacting said activated polymer with said aminoalkyl- or hydroxyalkyl-tannin.

23. A method of preparing a water-insoluble tannin preparation consisting essentially of tannin bound by covalent linkage to a water-insoluble, hydrophilic carrier selected from the group consisting of an amino-polymer and a carboxyl-polymer, which comprises:

(A) reacting tannin with cyanogen halide, epihalohydrin, α,ω-bis(2,3-epoxypropyl)alkane or α,ω-bis(2,3-epoxypropoxy)alkane to give an activated tannin, reacting said activated tannin with alkylenediamine or amino-carboxylic acid to give an aminoalkyl- or carboxyalkyl-tannin, and (B) reacting the aminoalkyl-tannin with the carboxyl-polymer; or reacting the carboxyalkyl-tannin with the amino-polymer.

24. The method of claim 20 wherein the hydroxy-polymer is polysaccharide or hydroxyalkyl-polysaccharide, and the amino-polymer is aminoalkyl-polysaccharide or aminobenzyl-polysaccharide.

25. The method of claim 21 wherein the amino-polymer is aminobenzyl-polysaccharide.

26. The method of claim 22 wherein the hydroxy-polymer is polysaccharide or hydroxyalkyl-polysaccharide, and the amino-polymer is aminoalkyl-polysaccharide or aminobenzyl-polysaccharide.

27. The method of claim 23 wherein the amino-polymer is aminoalkyl-polysaccharide or aminobenzyl-polysaccharide, and the carboxyl-polymer is carboxyalkyl-polysaccharide.

28. The method of claim 20 wherein said tannin is pyrogallol tannin.

29. The method of claim 21 wherein said tannin is pyrogallol tannin.

30. The method of claim 22 wherein said tannin is pyrogallol tannin.

31. The method of claim 23 wherein said tannin is pyrogallol tannin.

32. An immobilized protein consisting essentially of a biologically active protein adsorbed physically by a water-insoluble tannin preparation, said preparation consisting essentially of tannin covalently bound to a water-insoluble, hydrophilic carrier selected from a hydroxy-polymer, an amino-polymer and a carboxyl-polymer through a diazo linkage or by means of at least one of cyanogen halide, epihalohydrin, α,ω-bis(2,3-epoxypropyl)alkane and α,ω-bis(2,3-epoxypropoxy)alkane.

33. The immobilized protein of claim 32 wherein said cyanogen halide, epihalohydrin, α,ω-bis(2,3-epoxypropyl)-alkane and α,ω-bis(2,3-epoxypropoxy)alkane are employed in combination with at least one of alkylenediamine, aminoalkanol, aminoalkanoic acid, alkylenediol and haloalkanoyl halide.

34. An immobilized protein consisting essentially of a catalytically active enzyme adsorbed physically by a water-insoluble tannin preparation, said preparation consisting essentially of tannin covalently bound to a water-insoluble, hydrophilic carrier selected from a hydroxy-polymer, an amino-polymer and a carboxyl-polymer through a linkage selected from the group consisting of —CONH—, —CH$_2$CH(OH)CH$_2$—, —CH$_2$CH(OH)CH$_2$—A—CH$_2$CH(OH)CH$_2$—, —Y'λ—(CH$_2$)$_n$—NHCO—, —Y'—(CH$_2$)$_n$—CONH—, —Y'λ—(CH$_2$)$_n$NHCH$_2$CH(OH)CH$_2$—, —Y'λ—(CH$_2$)$_n$NH(CH$_2$)$_m$CO— and —CONH(CH$_2$)-$_n$OCH$_2$CH(OH)CH$_2$—, wherein Y' is —CONH— or —CH$_2$CH(OH)CH$_2$NH—, A is —(CH$_2$)$_q$— or —O(CH$_2$)$_q$O—, each one of $n$ and $m$ is an integer of 1 to 16 and $q$ is an integer of 1 to 6.

35. An immobilized protein consisting essentially of a catalytically active enzyme adsorbed physically by a water-insoluble tannin preparation, said preparation consisting essentially of tannin covalently bound to a water-insoluble, hydrophilic carrier selected from a hydroxy-polymer, an amino-polymer and a carboxyl-polymer through a linkage selected from the group consisting of —CH$_2$CH(OH)CH$_2$—, —CH$_2$CH(OH)CH$_2$—A—CH$_2$CH(OH)CH$_2$—, —CH$_2$CH(OH)CH$_2$NH(CH$_2$)$_n$—Y—, —CONH(CH$_2$)$_n$—Y—, —Y'—(CH$_2$)$_n$CONH(CH$_2$)$_m$—Y—, —Y'—(CH$_2$)$_n$NHCO(CH$_2$)$_m$—Y—,

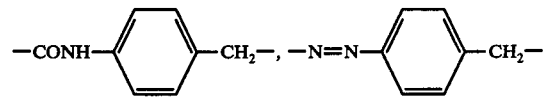

and

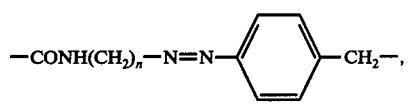

wherein Y is —NHCO—, —NHCH$_2$CH(OH)CH$_2$—, —OCH$_2$CH(OH)CH$_2$— or —NHCOCH$_2$—, Y' is is —CONH— or —CH$_2$CH(OH)CH$_2$NH—, each one of $n$ and $m$ is an integer of 1 to 16, A is —(CH$_2$)$_q$— or —O(CH$_2$)$_q$O—, and $q$ is an integer of 1 to 6.

36. An immobilized protein consisting essentially of a biologically active protein adsorbed physically by a water-insoluble tannin preparation, said preparation consisting essentially of tannin bound by physical adsorption to a polysaccharide derivative taken from the class consisting of:

Polysaccharide—O—CH$_2$CH(OH)CH$_2$O(CH$_2$)$_m$H,
Polysaccharide—O—CH$_2$CH(OH)CH$_2$NH(CH$_2$)$_m$H,
Polysaccharide—O—CONH(CH$_2$)$_m$H,

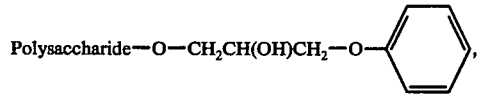

Polysaccharide—O—CH$_2$CH(OH)CH$_2$NH(CH$_2$)$_m$NH$_2$, and
Polysaccharide—O—CH$_2$CONH(CH$_2$)$_m$NH$_2$
wherein m is an integer of 1 to 16.

37. A method of preparing an immobilized protein which comprises:
(A) contacting a biologically active protein with a water-insoluble tannin preparation in an aqueous solvent, said tannin preparation consisting essentially of tannin covalently bound to a water-insoluble, hydrophilic carrier selected from a hydroxypolymer, an amino-polymer and a carboxyl-polymer through a diazo linkage or by means of at least one of cyanogen halide, epihalohydrin, α,ω-bis(2,3-epoxypropyl)alkane and α,ω-bis(2,3-epoxypropoxy)alkane,
(B) permitting said protein to be adsorbed on said tannin preparation, and
(C) recovering the resultant immobilized protein.

38. A method of preparing an immobilized protein which comprises:
(A) contacting a biologically active protein with a water-insoluble tannin preparation in an aqueous solvent, said tannin preparation consisting essentially of tannin covalently bound to a water-insoluble, hydrophilic carrier selected from a hydroxypolymer, an amino-polymer and a carboxyl-polymer, by means of at least one of cyanogen halide, epihalohydrin, α,ω-bis(2,3-epoxypropyl)alkane and α,ω-bis(2,3-epoxypropyl)alkane and α,ω-bis(2,3-epoxypropoxy)alkane in combination with at least one of alkylenediamine, aminoalkanol, aminoalkanoic acid, alkylenediol and haloalkanoyl halide,
(B) permitting said protein to be adsorbed on said tannin preparation, and
(C) recovering the resultant immobilized protein.

39. A method of preparing an immobilized protein which comprises:
(A) contacting a catalytically active enzyme with a water-insoluble tannin preparation in an aqueous solvent, said tannin preparation consisting essentially of tannin covalently bound to a water-insoluble, hydrophilic carrier selected from a hydroxypolymer, an amino-polymer and a carboxyl-polymer through a linkage selected from the group consisting of —CONH—, —CH$_2$CH(OH)CH$_2$—, —CH$_2$CH(OH)CH$_2$—A—CH$_2$CH(OH)CH$_2$—, —Y'—(CH$_2$)$_n$—NHCO—, —Y'—(CH$_2$)$_n$—CONH—, —Y'—(CH$_2$)$_n$—NHCH$_2$CH(OH)CH$_2$—, —Y'—(CH$_2$)$_n$NH(CH$_2$)$_m$CO— and —CONH(CH$_2$)$_n$OCH$_2$CH(OH)CH$_2$—, wherein Y' is —CONH— or —CH$_2$CH(OH)CH$_2$NH—, A is —(CH$_2$)$_q$— or —O(CH$_2$)$_q$O—, each one of n and m is an integer of 1 to 16 and q is an integer of 1 to 6,
(B) permitting said enzyme to be adsorbed on said tannin preparation, and
(C) recovering the resultant immobilized enzyme.

40. A method of preparing an immobilized protein which comprises:
(A) contacting a catalytically active enzyme with a water-insoluble tannin preparation in an aqueous solvent, said tannin preparation consisting essentially of tannin covalently bound to a water-insoluble, hydrophilic carrier selected from a hydroxypolymer, an amino-polymer and a carboxyl-polymer through a linkage selected from the group of consisting of —CH$_2$CH(OH)CH$_2$—, —CH$_2$CH(OH)CH$_2$—A—CH$_2$CH(OH)CH$_2$—, —CH$_2$CH(OH)CH$_2$NH(CH$_2$)$_n$—Y—, —CONH(CH$_2$)$_n$—Y—, —Y'—(CH$_2$)$_n$CONH(CH$_2$)$_m$—Y—, —Y'λ—(CH$_2$)$_n$NHCO(CH$_2$)$_m$—Y—,

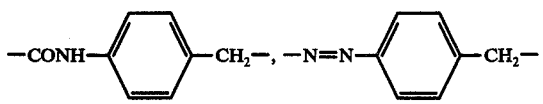

and

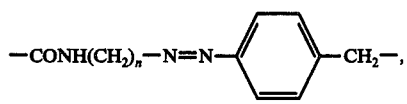

wherein Y is —NHCO—, —NHCH$_2$CH(OH)CH$_2$—, —OCH$_2$CH(OH)CH$_2$— or —NHCOCH$_2$—, Y' is —CONH— or —CH$_2$CH(OH)CH$_2$NH—, each one of n and m is an integer of 1 to 16, A is —(CH$_2$)$_q$— or —O(CH$_2$)$_q$O—, and q is an integer of 1 to 6,
(B) permitting said enzyme to be adsorbed on said tannin preparation, and
(C) recovering the resultant immobilized enzyme.

41. A method of preparing an immobilized protein which comprises:
(A) contacting a biologically active protein with a water-insoluble tannin preparation in an aqueous solvent, said tannin preparation consisting essentially of tannin bound by physical adsorption to a water-insoluble, hydrophilic carrier selected from the group consisting of:
Polysaccharide—O—CH$_2$CH(OH)CH$_2$O(CH$_2$)$_m$H,
Polysaccharide—O—CH$_2$CH(OH)CH$_2$NH(CH$_2$)$_m$H,
Polysaccharide—O—CONH(CH$_2$)$_m$H,

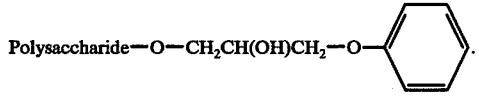

Polysaccharide—O—CH$_2$CH(OH)CH$_2$NH(CH$_2$)$_m$NH$_2$, and
Polysaccharide—O—CH$_2$CONH(CH$_2$)$_m$NH$_2$
wherein m is an integer of 1 to 16,
(B) permitting said protein to be adsorbed on said tannin preparation, and
(C) recovering the resultant immobilized protein.

* * * * *